US008487105B2

(12) United States Patent
Reddy et al.

(10) Patent No.: US 8,487,105 B2
(45) Date of Patent: Jul. 16, 2013

(54) PROCESS FOR PREPARING PITAVASTATIN, INTERMEDIATES AND PHARMACEUCTICALLY ACCEPTABLE SALTS THEREOF

(75) Inventors: Manne Satyanarayana Reddy, Hyderabad (IN); Sajja Eswaraiah, Hyderabad (IN); Maramreddy Sahadeva Reddy, Hyderabad (IN)

(73) Assignee: MSN Laboratories Limited, Hyderabad, Andhra Pradesh (IN)

( * ) Notice: Subject to any disclaimer, the term of this patent is extended or adjusted under 35 U.S.C. 154(b) by 0 days.

(21) Appl. No.: 13/145,089

(22) PCT Filed: Jan. 18, 2010

(86) PCT No.: PCT/IN2010/000029
§ 371 (c)(1),
(2), (4) Date: Sep. 7, 2011

(87) PCT Pub. No.: WO2010/089770
PCT Pub. Date: Aug. 12, 2010

(65) Prior Publication Data
US 2012/0016129 A1  Jan. 19, 2012

(30) Foreign Application Priority Data
Jan. 19, 2009  (IN) .......................................... 120/09

(51) Int. Cl.
*C07D 215/04* (2006.01)
(52) U.S. Cl.
USPC ........................................................ 546/173
(58) Field of Classification Search
None
See application file for complete search history.

(56) References Cited

U.S. PATENT DOCUMENTS

| 4,739,073 | A | 4/1988 | Kathawala |
| 4,970,313 | A | 11/1990 | Wess et al. |
| 4,977,279 | A | 12/1990 | Wess et al. |
| 5,260,440 | A | 11/1993 | Hirai et al. |
| 5,273,995 | A | 12/1993 | Roth |
| 5,354,772 | A | 10/1994 | Kathawala |
| 5,753,675 | A | 5/1998 | Wattanasin |
| 5,763,675 | A | 6/1998 | Levin |
| 5,856,336 | A | 1/1999 | Fujikawa et al. |
| 6,316,460 | B1 | 11/2001 | Creekmore et al. |
| 6,627,636 | B2 | 9/2003 | Robl |
| 6,835,838 | B2 * | 12/2004 | Chen et al. ..................... 546/173 |
| 6,841,554 | B2 | 1/2005 | Taylor et al. |
| 6,844,437 | B1 | 1/2005 | Taylor et al. |
| 6,875,867 | B2 | 4/2005 | Brodfuehrer et al. |
| 7,312,329 | B2 | 12/2007 | Joshi et al. |
| 7,371,865 | B2 * | 5/2008 | Acemoglu et al. ............. 546/173 |
| 2004/0049036 | A1 | 3/2004 | Taylor et al. |
| 2004/0176401 | A1 | 9/2004 | Matsushita et al. |
| 2005/0080134 | A1 | 4/2005 | Niddam-Hildesheim et al. |
| 2005/0124639 | A1 | 6/2005 | Joshi et al. |
| 2005/0209259 | A1 | 9/2005 | Huang |
| 2006/0004200 | A1 | 1/2006 | Gudipati et al. |
| 2009/0275752 | A1 | 11/2009 | Reddy et al. |
| 2010/0056783 | A1 | 3/2010 | Reddy et al. |

FOREIGN PATENT DOCUMENTS

| CN | 1821242 A | 8/2006 |
| CN | 101386592 A | 3/2009 |
| EP | 0 304 063 B1 | 11/1994 |
| EP | 1 099 694 B1 | 8/2005 |
| JP | 6041114 A | 5/1994 |
| WO | WO 95/11898 | 5/1995 |
| WO | WO 95/13283 | 5/1995 |
| WO | WO 97/19917 | 6/1997 |
| WO | WO 98/32751 | 7/1998 |
| WO | WO 99/11258 | 3/1999 |
| WO | WO 99/45003 | 9/1999 |
| WO | WO 01/60804 A1 | 8/2001 |
| WO | WO 02/09697 A1 | 2/2002 |
| WO | WO 02/092570 A1 | 11/2002 |
| WO | WO 02/094804 A1 | 11/2002 |
| WO | WO 03/006439 A1 | 1/2003 |
| WO | WO 03/016317 A1 | 2/2003 |
| WO | WO 03/045935 A1 | 6/2003 |
| WO | WO 03/070717 A1 | 8/2003 |
| WO | WO 03/097614 A2 | 11/2003 |
| WO | WO 2004/014872 A1 | 2/2004 |
| WO | WO 2004/108691 A1 | 12/2004 |
| WO | WO 2005/033083 A1 | 4/2005 |
| WO | WO 2005/040134 A1 | 5/2005 |
| WO | WO 2005/042522 A1 | 5/2005 |
| WO | WO 2005/054207 A1 | 6/2005 |
| WO | WO 2005/077916 A1 | 8/2005 |
| WO | WO 2006/035277 A2 | 4/2006 |
| WO | WO 2006/079611 A1 | 8/2006 |
| WO | WO 2006/136407 A1 | 12/2006 |
| WO | WO 2007/000121 A1 | 1/2007 |
| WO | WO 2007/040940 A1 | 4/2007 |

(Continued)

OTHER PUBLICATIONS

International Search Report from counterpart International Application No. PCT/IN2010/000029, dated Aug. 26, 2010.
Johnson, Douglas S. , "The Art of Drug Synthesis", *Synthesis of Pitavastatin (Livalo®)*, pp. 177-179, ISBN: 15978-0-471-75215-8 (2007).
Cai, Zhengyan et al., "Synthesis of Pitavastatin Calcium", *Chinese Journal of Pharmaceuticals*, 28(38): 178-179 (2007).
International Preliminary Report on Patentability from International Application No. PCT/IN2007/000459, titled "Novel Process for the Preparation of Statins and Their Pharmaceutically Acceptable Salts Thereof", dated Aug. 4, 2010.

(Continued)

*Primary Examiner* — Janet Andres
*Assistant Examiner* — Timothy R Rozof
(74) *Attorney, Agent, or Firm* — Hamilton, Brook, Smith & Reynolds, P.C.

(57) ABSTRACT

Processes for preparing pravastatin, intermediates and pharmaceutically acceptable salts thereof are provided Crystalline forms of pravastatin, intermediates and pharmaceutically acceptable salts thereof are also disclosed.

22 Claims, 4 Drawing Sheets

FOREIGN PATENT DOCUMENTS

| | | |
|---|---|---|
| WO | WO 2007/041666 A1 | 4/2007 |
| WO | WO 2007/052309 A2 | 5/2007 |
| WO | WO 2007/086082 A2 | 8/2007 |
| WO | WO 2007/086082 A3 | 8/2007 |
| WO | WO 2007/100351 A2 | 9/2007 |
| WO | WO 2007/125547 A2 | 11/2007 |
| WO | WO 2007/125547 A3 | 11/2007 |
| WO | WO 2007/132482 A2 | 11/2007 |
| WO | WO 2007/132482 A3 | 11/2007 |
| WO | WO 2008/044243 A2 | 4/2008 |
| WO | WO 2008/044243 A3 | 4/2008 |
| WO | WO 2010/023678 A1 | 3/2010 |
| WO | WO 2011/086584 A2 | 7/2011 |

OTHER PUBLICATIONS

Written Opinion of the International Searching Authority from International Application No. PCT/IN2007/000459, titled "Novel Process for the Preparation of Statins and Their Pharmaceutically Acceptable Salts Thereof", dated Dec. 3, 2009.

International Search Report for International Application No. PCT/IN2007/000459, titled "Novel Process for the Preparation of Statins and Their Pharmaceutically Acceptable Salts Thereof", dated Dec. 3, 2009.

Author unknown, "Process for the preparation of 2, 2-dimethyl-1, 2, 3, 7, 8, 8a-hexahydro-3, 7-dimethyl-8-[2-tetrahydro-4-hydroxy-6-oxo-2H-pyran-2-y1)-ethyl]-1-napthalenyl ester and intermediates thereof", *IP.com Journal*, vol. 6(10A), 2 (No. IPCOM000140631D) compounds of formula IV (Sep. 17, 2006).

Patel, D.S., et al., "Process for preparation of 2,2-dimethylbutyric acid 8-ester of [1,2,6,7,8, 8a(R)-hexahydro-2(S) ,6(R)-dimethyl-1(S)-naphthylethyl] tetrahydro-4-hydroxy-2H-pyran-2-one from broth containing [1,2,6,7, 8,8a(R)-hexahydro-2(S) ,6(R)dimethyl-8(S)methyl-1-oxobutoxy-1-naphthyl]-3(R)   ,5 (R)dihydroxyheptanoic acid", (abstract) Database CA [Online] Chemcial Abstracts Service Columbus, Ohio, US; Retrieved from STN International, Columbus, Ohio, USA. Accession No. 148:403004 RN 1015249-88-3 (2007).

Brousseau, M.E., et al., "Structure and mechanism of action of HMG-CoA reductase inhibitors", The British Library—"The World's Knowledge", pp. 19-34, ed. By Gerd Schmitz and Michael Torzewski, Birkhauser (2002).

International Search Report for PCT/IN2007/000172, titled "Novel Process for Statins and Its Pharmaceutically Acceptable Salts Thereof", dated Jan. 18, 2008.

International Preliminary Report on Patentability from International Application No. PCT/1N2007/000172, titled "Novel Process for Statins and Its Pharmaceutically Acceptable Salts Thereof", dated Jun. 16, 2008.

Written Opinion of the International Preliminary Examining Authority from International Application No. PCT/IN2007/000172, titled "Novel Process for Statins and Its Pharmaceutically Acceptable Salts Thereof", dated Jan. 18, 2008.

Miyachi, N., et al., "A Novel Synthetic Method of HMG-CoA Reductase Inhibitor NK-104 Via A Hydroboration-Cross Coupling Sequence", *Tetrahedron Letters*, 34(51):8267-8270 (1993).

Wess, G., et al., "Stereoselective Synthesis of HR 780 A New Highly Potent HMG-COA Reductase Inhibitor", *Tetrahedron Letters*, 31(18):2545-2548 (1990).

Takahashi, Kyoko, et al., "Synthesis of an Artificial HMG-CoA Reductase Inhibitor NK-104 via a Hydrosilylation—Cross-Coupling Reaction", *Bull. Chem. Soc. Jpn.*, 68:2649-2656 (1995).

Written Opinion of the International Searching Authority for International Application No. PCT/IN2010/000029, titled "Processes for Preparing Pitavastatin, Intermediates and Pharmaceutically Acceptable Salts Thereof", dated Aug. 26, 2010.

International Preliminary Report on Patentability for International Application No. PCT/IN2010/000029, titled "Processes for Preparing Pitavastatin, Intermediates and Pharmaceutically Acceptable Salts Thereof", dated Jul. 19, 2011.

Written Opinion of the International Searching Authority for International Patent Application No. PCT/IN2010/000029 dated Aug. 26, 2010.

International Preliminary Report on Patentability for International Patent Application No. PCT/IN2010/000029 dated Jul. 19, 2011.

Minami, T., et al., "Stereoselective Reduction of β-δ-Diketo Esters Derived from Tartaric Acid. A Facile Route to Optically Active 6-OXO-3,5-*syn*-Isopropylidenedioxyhexanoate, a Versatile Synthetic Intermediate of Articicial HMG Co-A Reductase Inhibitors", *Tetrahedron Letters*, 34(3):513-516 (1993).

\* cited by examiner

MSN Laboratories Limited

PROCESS FOR PREPARING PITAVASTATIN, INTERMEDIATES AND PHARMACEUCTICALLY ACCEPTABLE SALTS THEREOF

RELATED APPLICATIONS

This application is the U.S. National Stage of International Application No. PCT/IN2010/000029, filed Jan. 18, 2010, which designates the U.S., published in English, and claims priority under 35 U.S.C. §§119 or 365(c) to IN Application No. 120/CHE/2009, filed Jan. 19, 2009, which are incorporated herein by reference.

FIELD OF THE INVENTION

The present invention relates to an improved process for the preparation of highly pure (3R,5S)-7-[2-cyclopropyl-4-(4-fluorophenyl)quinolin-3-yl]-3,5-dihydroxy-6(E)-heptenoic acid and generally known as Pitavastatin. Pitavastatin and its pharmaceutically acceptable salts are represented by the following general structural formula-1.

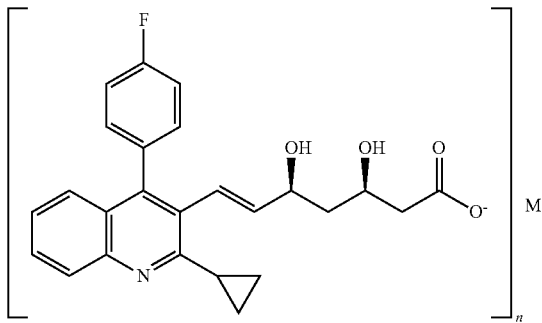

Formula-1

Wherein n=1, M is $H^+$, $Na^+$, $K^+$
n=2, M is $Mg^{+2}$, $Ca^{+2}$

Pitavastatin is a synthetic lipid-lowering agent that acts as an inhibitor of 3-hydroxy-3-methylglutaryl-coenzyme A reductase (HMG-CoA reductase inhibitor). This enzyme catalyzes the conversion of HMG-CoA to mevalonate. The HMG-CoA reductase inhibitors are commonly referred to as "statins". Statins are therapeutically effective drugs used for reducing low density lipoprotein (LDL) particle concentration in the blood stream of patients who are at risk for cardiovascular disease. Pitavastatin is used in the treatment of hypercholesterolemia (heterozygous familial and nonfamilial) and mixed dyslipidemia (Fredrickson Type IIa and IIb).

The compound of the present invention inhibits the HMG-CoA reductase, which plays a main role in the synthesis of cholesterol, and as a consequence they suppress the biosynthesis of cholesterol. Therefore, they are useful in the treatment of hypercholesterolemia, hyperlipoproteinemia, and atherosclerosis.

BACKGROUND OF THE INVENTION

U.S. Pat. No. 5,856,336 claimed quinoline type mevalonolactones, specifically pitavastatin. The disclosed process involves the usage of expensive reagents like sodium hydride, n-butyl lithium and borane derivatives, reagents that are difficult to use on a commercial scale.

International publication WO 95/11898 claims a process for the preparation of condensed pyridine type mevalonolactone intermediates using wittig reagent. In the said process the triphenyl phosphonium bromide intermediate compound of formula-7 was condensed with tertiary butyl 2-((4R,6S)-6-formyl-2,2-dimethyl-1,3-dioxan-4-yl)acetate compound of formula-8 in presence of n-BuLi. And the said patent discloses a process for the preparation of lactone intermediate but the conversion of lactone intermediate to pitavastatin calcium salt has not been disclosed. The usage of bases like n-BuLi is not recommendable for commercial scale up processes. Hence this process is commercially not a viable process.

International publication WO 2005/033083 claims process for the preparation of pure 3,5-dihydroxy-6-heptenoic acid derivatives by optical resolution using column separation process, which is not viable of commercial scale.

Other than the above international publication WO 2005/054207 claims process for the preparation of pyrimidine derivatives and its intermediates using wittig reagent; Our international application WO 2007/132482 claims a novel process for the preparation of pitavastatin and its pharmaceutically acceptable salts using wittig reaction. Another international publication WO 2007/125547 claims a process for the preparation of statins free of Z-isomer via julia-olefination.

Polymorphism is the formation of a variety of crystalline forms of the same compound having distinct crystal structures and physical properties like melting points, X-ray diffraction pattern, infrared absorption pattern in fingerprint region, and solid state NMR spectrum. One crystalline form may give rise to thermal behavior different from that of another crystalline form. Different crystalline forms or polymorphs of the same pharmaceutical compounds can and reportedly do have different aqueous solubility. The difference in the physical properties of different crystalline forms results in some forms having distinct advantageous physical properties compared to other crystalline forms of the same compound. The discovery of new polymorphic forms of pharmaceutically useful compounds provides a new opportunity to improve the performance characteristics of a pharmaceutical product. Those skilled in the art can understand that crystallization of an active pharmaceutical ingredient offers the best method for controlling important qualities like chemical quality, particle size, and polymorphic content. There is a need in the art for the preparation of new polymorphic forms of Pitavastatin and its pharmaceutically acceptable salts, and the intermediates which are used in the preparation of pitavastatin and its pharmaceutically acceptable salts.

Accordingly, there remains a need for an improved process for the preparation of pitavastatin and its pharmaceutically acceptable salts that avoids the problems of the prior art, on a commercial scale in a convenient and cost efficient manner.

BRIEF DESCRIPTION OF THE INVENTION

The present invention relates to an improved process for the preparation of pitavastatin and its pharmaceutically acceptable salts, compounds of general formula-1, preferably calcium salt, compound of formula-1c.

The first aspect of the present invention provides an improved process for the preparation of pitavastatin and its pharmaceutically acceptable salts, compounds of general formula-1, preferably pitavastatin calcium compound of formula-1c, which comprises of the following steps;

a) Reacting the triphenyl [2-cyclopropyl-4-(4-fluorophenyl)-quinoline-3-yl-methyl)-phosphonium]bromide compound of formula-2 with tertiary butyl 24(4R,6S)-6-formyl-2,2-dimethyl-1,3-dioxan-4-yl)acetate compound of formula-3 in presence of suitable base in a suitable solvent, followed by recrystallisation from a suitable solvent, to provide (4R,6S)-(E)-6-{2-(2-cyclopropyl-4-(4-fluorophenyl)quinolin-3-yl)-vinyl]-2,2-dimethyl[1,3]-dioxan-4-yl]-acetic acid tertiary butyl ester compound of formula-4,
b) subjecting compound of formula-4 to acidic conditions to remove the acetonide protection, followed by recrystallisation from a suitable solvent, to provide pitavastatin tertiary butyl ester compound of formula-5,
c) hydrolyzing the pitavastatin tertiary butyl ester compound of formula-5 with a suitable base in a suitable solvent, subsequent treatment with a suitable organic amine, followed by recrystallisation from a suitable solvent to provide corresponding organic amine salt of pitavastatin compound of general formula-6,
d) treating the organic amine salt compound of general formula-6 with a suitable base to provide corresponding alkali metal salt of pitavastatin, which on treating in-situ with calcium source to provide pitavastatin calcium compound of formula-1c.

The second aspect of the present invention provides an improved process for the preparation of pitavastatin and its pharmaceutically acceptable salt compound of general formula-1, preferably pitavastatin calcium salt compound of formula-1c, which comprises of the following steps a) Reacting the triphenyl [2-cyclopropyl-4-(4-fluorophenyl)-quinoline-3-yl-methyl)-phosphonium]bromide compound of formula-2 with tertiary butyl 2-((4R,6S)-6-formyl-2,2-dimethyl-1,3-dioxan-4-yl)acetate compound of formula-3 in presence of a suitable base in a suitable solvent, followed by recrystallisation from a suitable solvent, to provide (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester compound of formula-4,
b) subjecting compound of formula-4 to acidic conditions to remove the acetonide protection, followed by recrystallisation from a suitable solvent, to provide pitavastatin tertiary butyl ester compound of formula-5,
c) hydrolyzing pitavastatin tertiary butyl ester with a suitable aqueous base to provide corresponding alkali salt of pitavastatin, which on treating in-situ with a calcium source to provide pitavastatin calcium compound of formula-1c.

The third aspect of the present invention provides an improved process for the preparation of highly pure triphenyl [2-cyclopropyl-4-(4-fluorophenyl)-quinoline-3-yl-methyl)-phosphonium]bromide compound of formula-2, which comprises of the following steps;

a) Reacting cyclopropyl methyl ketone compound of formula-7 with dimethylcarbonate in presence of a suitable base in a suitable solvent to provide methyl 3-cyclopropyl-3-oxopropanoate compound of formula-8,
b) reacting the compound of formula-8 with 2-amino-4'-fluorobenzophenone compound of formula-9 in presence of an acid with or without a solvent to provide methyl 2-cyclopropyl-4-(4-fluorophenyl)quinoline-3-carboxylate compound of formula-10,
c) reducing the compound of formula-10 with a suitable reducing agent in a suitable solvent, followed by recrystallisation from a suitable solvent, to provide a (2-cyclopropyl-4-(4-fluorophenyl)quinoline-3-yl]methanol compound of formula-11,
d) reacting the compound of formula-11 with phosphorous tribromide in a suitable solvent, subsequent treatment with triphenyl phosphene in a suitable solvent, followed by recrystallisation from a suitable solvent to provide triphenyl [2-cyclopropyl-4-(4-fluorophenyl)-quinoline-3-yl-methyl)-phosphonium]bromide compound of formula-2.

The fourth aspect of the present invention is to provide crystalline form of (4R,6S)-(E)-6-{2-(2-cyclopropyl-4-(4-fluorophenyl)quinolin-3-yl)-vinyl]-2,2-dimethyl-[1,3]-dioxane-4-yl}-acetic acid tertiary butyl ester compound of formula-4.

The further aspects of the present invention provides crystalline forms of pitavastatin tertiary butyl ester compound of formula-5, pitavastatin methyl amine salt compound of formula-6a; pitavastatin compound of formula-1a; pitavastatin sodium compound of formula-1b.

Advantages of the Present Invention

Economical and commercially viable process
Involves the usage of inexpensive raw materials, such as triphenyl phosphine and alkali/alkaline earth metal bases like carbonate bases.
Avoids the usage of wittig-Horner type reagent and pyrophoric n-butyl lithium, which are not recommendable on commercial scale.
The present invention provides highest purity of pitavastatin and its intermediates by removing/controlling the impurities by simple purification technique at origin of the impurities.
The present invention provides crystalline form of triphenyl [2-cyclopropyl-4-(4-fluorophenyl)-quinoline-3-yl-methyl)-phosphonium]bromide salt as well as crystalline forms of dihydroxy tertiary butyl ester, pitavastatin methyl amine, pitavastatin free acid and pitavastatin sodium.

DETAILED DESCRIPTION OF THE INVENTION

Figure 1A:
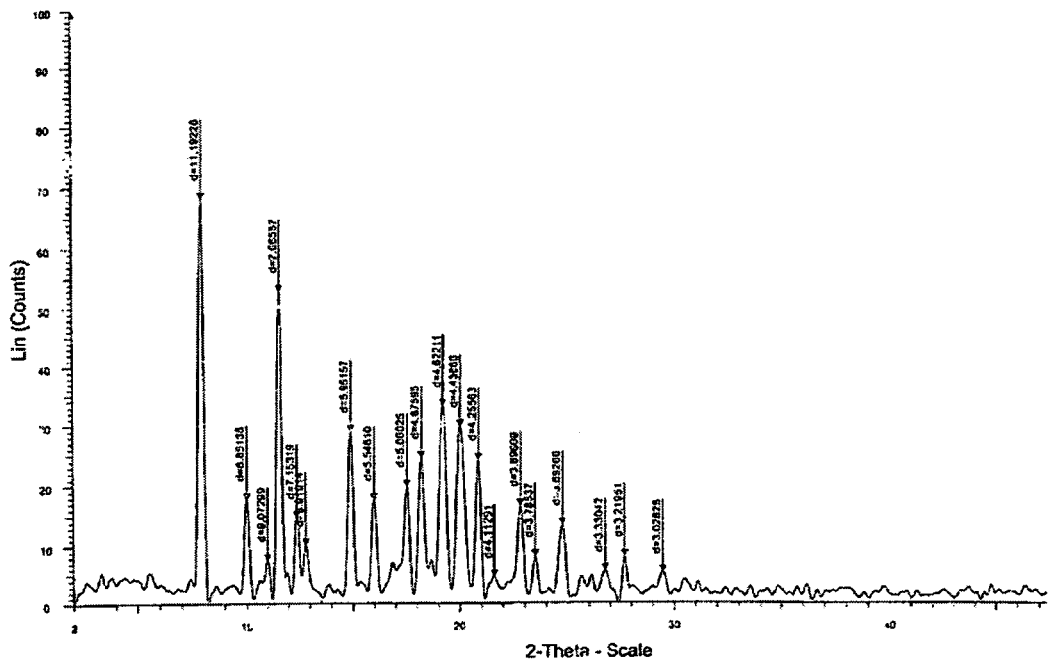
FIG. 1a: Illustrates the Powder X-ray diffraction pattern of (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester compound of formula-4.

As used herein the term "alkyl" refers to straight or branched or cyclic $C_1$-$C_{12}$ alkyl; and the term "aryl" refers to $C_6$-$C_{12}$ aromatic group include phenyl, tolyl, xylyl, biphenyl, naphthyl and the like. The aryl may have 1 to 3 substituents independently selected from the group consisting of lower alkyl, halogen, amino, cyano, hydroxyl; and the term "aralkyl" refers to $C_1$-$C_6$ lower alkyl substituted $C_6$-$C_{12}$ aromatic aryl group defined above. For example are benzyl, phenylethyl, phenylpropyl and the like each of which may have 1 to 3 substituents independently selected from the group consisting of lower alkyl, halogen, amino, cyano, hydroxy and the like.

As used herein, the term "alcohol solvents" refers to methanol, ethanol, n-propanol, isopropanol and n-butanol and the like; "hydrocarbon solvents" refers to toluene, xylene, cyclohexane, hexane, heptane and the like; "polar aprotic solvents" refers to dimethylsulfoxide, dimethylacetamide, dimethyl formamide, tetrahydrofuran, acetonitrile and the like; "chloro solvents" refers to methylene chloride, ethylene dichloride, carbon tetra chloride, chloroform and the like; "nitrile solvents" refers to acetonitrile and the like;

As used, herein the term "alkali metal hydroxides" refers to sodium hydroxide, potassium hydroxide and the like; "alkali metal carbonates" refers to sodium carbonate, potassium carbonate, cesium carbonate and the like; "alkali metal bicarbonates" refers to sodium bicarbonate, potassium bicarbonate and the like; "alkali metal alkoxides" refers to sodium methoxide, sodium tertiary butoxide and potassium tertiary butoxide and the like.

As used herein the term "inorganic acids" refers to hydrochloric acid, hydrobromic acid, sulfuric acid and the like; the term: "organic acid" refers to acetic acid, oxalic acid, para toluene sulfonic acid, poly phospharic acid, methane sulphonic acid, maleic acid, malic acid, fumaric acid and formic acid.

As used herein the term "organic amines" refers to methyl amine, ethyl amine, n-propyl amine, isopropyl amine, n-butyl amine, tertiary butyl, (+/−)-sec-butyl amine, octyl amine, 2-ethyl hexylamine, benzyl amine, α-methyl-benzylamine, phenyl ethylamine, dibenzylamine, N-methylbenzylamine, N,N-dimethylbenzylamine, N,N-diethyl benzyl amine, N-ethyl-N-methylbenzylamine, tribenzyl amine, cyclopentylamine, cyclohexylamine, cycloheptylamine, N-methylcyclopentylamine, N-ethylcyclohexyl amine, N-ethyl cycloheptylamine, dicyclohexylamine, N,N-dimethylcyclo pentylamine, N,N-dimethyl cyclohexylamine, N,N-diethylcycloheptylamine and the like.

The present invention relates to an improved process for the preparation of pitavastatin and its pharmaceutically acceptable salt compounds represented by the following structural formula-1.

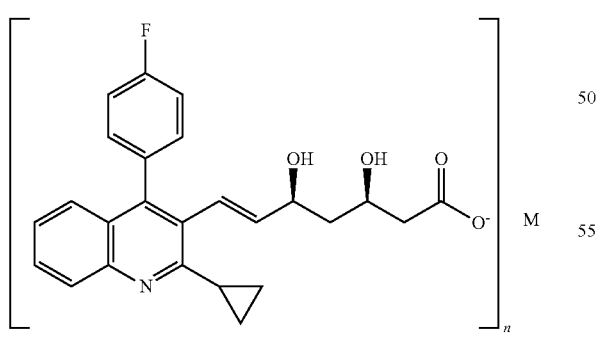

Formula-1

Wherein n=1, M is H⁺, Na⁺, K⁺
n=2, M is Mg⁺², Ca⁺²

Accordingly the first aspect of the present invention provides an improved process for the preparation of pitavastatin and its pharmaceutically acceptable salt compounds of general formula-1, preferably pitavastatin calcium salt compound of formula-1c,

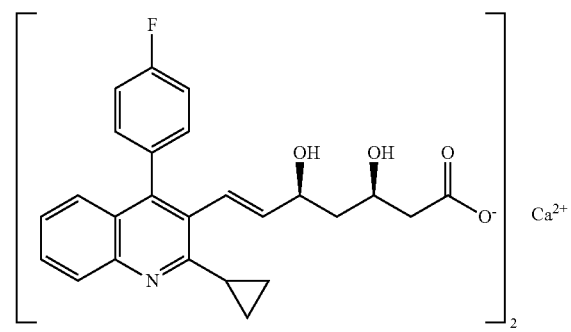

Formula-1c which comprises of the following steps;

a) reacting the triphenyl [2-cyclopropyl-4-(4-fluorophenyl)-quinoline-3-yl-methyl)-phosphonium]bromide salt compound of formula-2

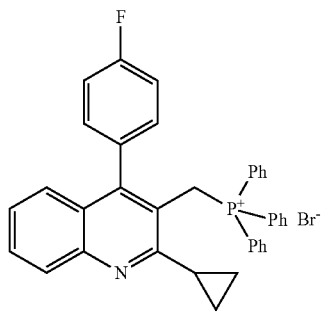

Formula-2 with tertiary butyl 2-((4R,6S)-6-formyl-2,2-dimethyl-1,3-dioxan-4-yl)acetate compound of formula-3

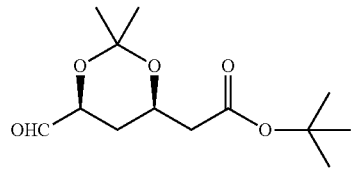

Formula-3 in presence of a base in a suitable solvent, followed by recrystallisation from a suitable solvent to provide (4R, 6S)-(E)-6-[2-(2-cyclopropyl-4-(4-fluorophenyl)quinolin-3-yl)-vinyl]-2,2-dimethyl[1,3]-dioxan-4-yl]-acetic acid tertiary butyl ester compound of formula-4, Formula-4

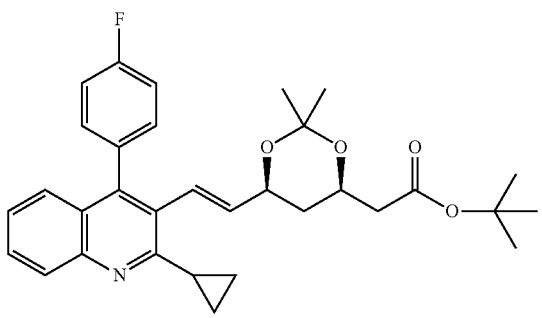

b) reacting (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester compound of formula-4 with an acid in a suitable solvent, followed by recrystallisation from a suitable solvent to provide pitavastatin tertiary butyl ester compound of formula-5, Formula-5

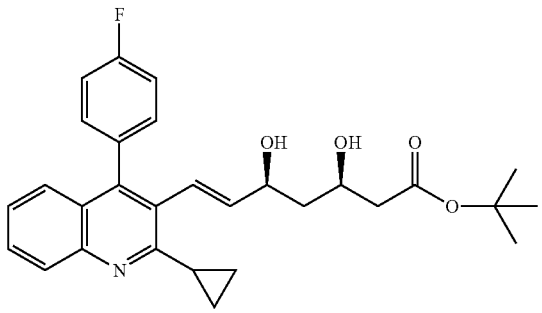

c) hydrolysis of pitavastatin tertiary butyl ester compound of formula-5 in presence of a suitable base in a suitable solvent, followed by subsequent treatment with a suitable organic amine, recrystallization of the obtained solid from a suitable solvent to provide corresponding pitavastatin organic amine salt compounds of general formula-6, Formula-6

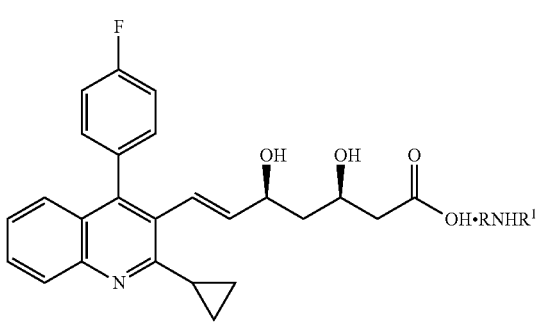

wherein R=alkyl or aryl or aralkyl or substituted aryl and R¹ is optionally hydrogen or alkyl or aryl or aryl alkyl or substituted aryl;

d) hydrolyzing the compound of general formula-6 with a suitable base in a suitable solvent to provide corresponding alkali metal salt of pitavastatin, which on treating in-situ with a calcium source to provide pitavastatin calcium salt compound of formula-1c.

The second aspect of the present invention is to provide an improved process for the preparation of pitavastatin or its pharmaceutically acceptable salt compound of general formula-1, preferably pitavastatin calcium salt compound of formula-1c, which comprises of the following steps;

a) reacting the triphenyl [2-cyclopropyl-4-(4-fluorophenyl)-quinoline-3-yl-methyl)-phosphonium]bromide salt compound of formula-2

Formula-2

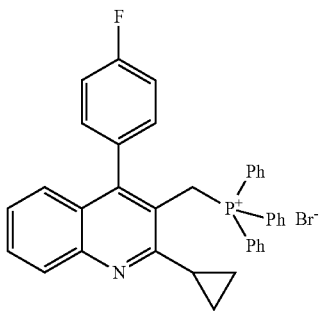

with tertiary butyl 2-((4R,6S)-6-formyl-2,2-dimethyl-1,3-dioxan-4-yl)acetate compound of formula-3

Formula-3

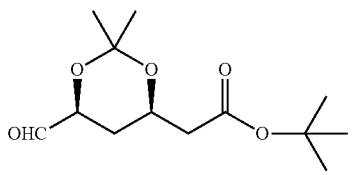

in presence of a base in a suitable solvent, followed by recrystallisation from a suitable solvent to provide (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester compound of formula-4, Formula-4

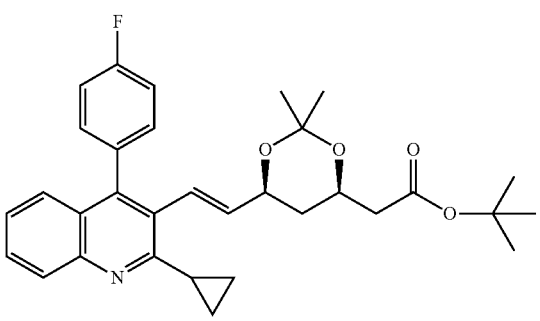

b) reacting (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester compound of formula-4 with a suitable acid in a suitable solvent, followed by recrystallisation from a suitable solvent to provide pitavastatin tertiary butyl ester compound of formula-5,

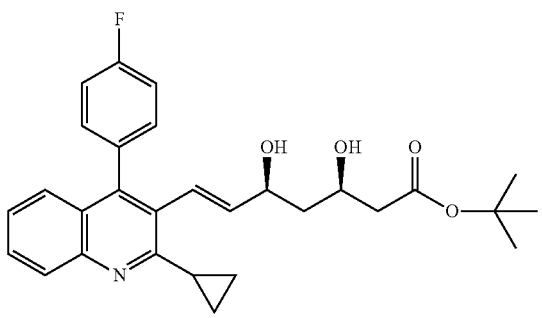

Formula-5 c) hydrolyzing the compound of general formula-5 with a suitable alkali metal base in a suitable solvent to provide corresponding alkali metal salt of pitavastatin, which on in-situ treatment with a calcium source to provide pitavastatin calcium compound of formula-1c.

Wherein in step a) of first and second aspect of the invention, the condensation of triphenyl[2-cyclopropyl-4-(4-fluorophenyl)-quinoline-3-ylmethyl)-phosphonium]bromide salt compound of formula-2 with tertiary butyl 2-((4R,6S)-6-formyl-2,2-dimethyl-1,3-dioxan-4-yl)acetate compound of formula-3, the base is selected from alkali metal hydroxides, alkali metal alkoxides or alkali metal carbonates or alkali metal bicarbonates, preferably alkali metal carbonate like potassium carbonate and the suitable solvent is selected from polar aprotic solvents or alcohol solvents preferably polar aprotic solvents like dimethylsulfoxide. Thus obtained compound of formula-4 is recrystallised from a suitable solvents selected from alcohols or hydrocarbons to remove the corresponding Z-isomer of the compound of formula-4, herein designated as "Impurity-A", preferably using alcoholic solvents like methanol.

In step b) of first and second aspect of the invention, the deprotection of acetonide in compound of formula-4 is carried out in presence of a suitable acid selected from inorganic acids or organic acids, preferably organic acids like oxalic acid in a suitable solvent selected from alcoholic solvents or hydrocarbon solvents, nitrile solvents, preferably alcoholic solvents like methanol to provide pitavastatin tertiary butyl ester compound of formula-5, which on further recrystallized from a suitable solvent like alcoholic solvents or hydrocarbon solvents, preferable hydrocarbon solvents like toluene, to remove the corresponding anti-isomer impurity compound of formula-5; herein designated as "Impurity-B".

In step c) of first aspect of the invention, the hydrolysis of pitavastatin tertiary butyl ester compound of formula-5 is carried out in presence of a base selected from alkali metal hydroxides or alkali metal carbonates or alkali metal bicarbonates, preferably alkali metal hydroxide like sodium hydroxide in presence of a suitable solvent selected from hydrocarbon solvents or polar aprotic solvents nitrile solvents, preferably acetonitrile to provide corresponding alkali metal salt of pitavastatin, which on in-situ treatment with suitable organic amine provides corresponding organic amine salt of pitavastatin compound of general formula-6. The obtained organic amine compound of general formula-6 is recrystallised from a suitable solvent selected from alcoholic solvents or hydrocarbon solvents or polar aprotic solvents or nitrile solvents, preferably nitrile solvent like acetonitrile to remove the formed lactone impurity herein designated as "Impurity-C" and there by controlling the formation of corresponding amide impurity herein designated as "Impurity-D".

In step d) of first aspect and step c) of the second aspect of the invention, hydrolysis of compound of general formula-6 or formula-5 with an alkali metal base selected from alkali metal hydroxides or alkali metal carbonates or alkali metal bicarbonates, preferably sodium hydroxide in presence of a polar solvent like water to provide corresponding alkali metal salt of pitavastatin, which on in-situ treatment with calcium source like calcium chloride, calcium acetate and calcium bromide, preferably calcium chloride to provide pitavastatin calcium salt compound of formula-1c.

Optionally the alkali metal salt of pitavastatin like potassium salt of pitavastatin and sodium salt of pitavastatin obtained in step d) of first aspect and step c) of second aspect of the invention are isolated as a crystalline solid. Thus obtained crystalline alkali metal salt can be converted into pitavastatin calcium compound of formula-1c.

The third aspect of the present invention provides, an improved process for the preparation of highly pure triphenyl [2-cyclopropyl-4-(4-fluorophenyl)-quinoline-3-ylmethyl)-phosphonium]bromide compound of formula-2,

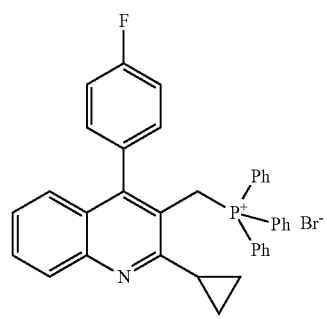

Formula-2 which comprises of the following steps;

a) reacting cyclopropyl methyl ketone compound of formula-7 with dimethyl carbonate in presence of a suitable base in a suitable solvent to provide a highly pure methyl 3-cyclopropyl-3-oxopropanoate compound of formula-8,

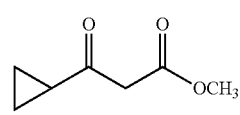

Formula-8 b) reacting the methyl 3-cyclopropyl-3-oxopropanoate compound of formula-8 with 2-amino-4'-fluorobenzophenone compound of formula-9,

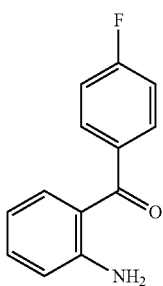

Formula-9 in presence of acid like sulfuric acid with or without a solvent to provide methyl 2-cyclopropyl-4-(4-fluorophenyl)quinoline-3-carboxylate compound of formula-10,

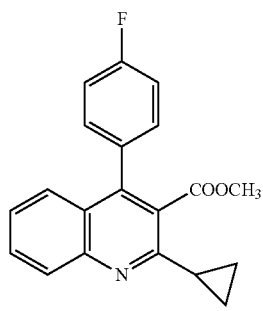

Formula-10 c) reducing the methyl 2-cyclopropyl-4-(4-fluorophenyl) quinoline-3-carboxylate compound of formula-10 with a suitable reducing agent in a suitable solvent, followed by recrystallisation from a suitable solvent to provide (2-cyclopropyl-4-(4-fluorophenyl)quinoline-3-yl)methanol compound of formula-11,

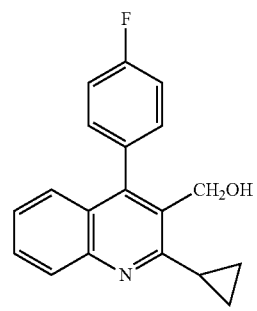

Formula -11 d) reacting (2-cyclopropyl-4-(4-fluorophenyl)quinoline-3-yl)methanol compound of formula-11 with phosphorous tribromide in a suitable solvent, subsequent treatment with triphenyl phosphene in a suitable solvent, followed by recrystallisation from a suitable solvent to provide pure triphenyl[2-cyclopropyl-4-(4-fluorophenyl)-quinoline-3-ylmethyl)-phosphonium]bromide salt compound of formula-2.

Wherein in step a) cyclopropyl methyl ketone compound of formula-7 on reaction with dimethyl carbonate in presence of a suitable base selected from alkali metal hydroxides or alkali metal alkoxides or alkali metal carbonates or alkali metal bicarbonates preferably potassium tertiary butoxide in a suitable solvent selected from hydrocarbon solvents, preferably toluene provides highly pure methyl 3-cyclopropyl-3-oxopropanoate compound of formula-8. The dicyclopropyl compound having the following structure (dicylcopropyl impurity) is formed as an impurity in this stage,

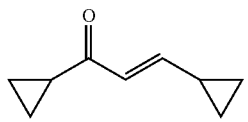

Dicyclopropyl impurity

Wherein in step b) the methyl 3-cyclopropyl-3-oxopropanoate compound of formula-8 reacting with 2-amino-4'-fluorobenzophenone compound of formula-9 in presence of a suitable acid selected from sulfuric acid, para toluene sulfonic acid, methane sulfonic acid and the like, with or without a solvent to provide methyl 2-cyclopropyl-4-(4-fluorophenyl) quinoline-3-carboxylate compound of formula-10. The suitable solvent used for this step is selected from alcoholic solvents or hydrocarbon solvents, preferably methanol.

Wherein in step c) the reduction of methyl 2-cyclopropyl-4-(4-fluorophenyl)quinoline-3-carboxylate compound of formula-10 is carried out with DIBAL-H or vitride in a suitable hydrocarbon solvent preferably toluene to provide (2-cyclopropyl-4-(4-fluorophenyl)quinoline-3-yl)methanol compound of formula-11, the obtained compound is recrystallized from a suitable solvent selected from hydrocarbon solvents, preferably cyclohexane to provide pure compound of formula-11 free of dihydro impurity having the following structural formula.

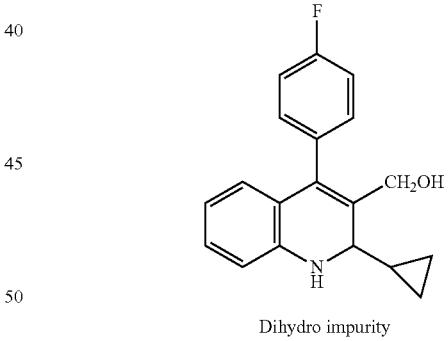

Dihydro impurity

Wherein in step d) (2-cyclopropyl-4-(4-fluorophenyl) quinoline-3-yl)methanol compound of formula-11 is reacted with phosphorous tribromide in a suitable chloro solvent, preferably methylene chloride to provide a bromo compound, which on subsequent reaction with the reagents like triphenyl phosphine, tributyl phosphine, preferably triphenyl phosphine in a suitable solvent selected from non-polar solvents such as toluene, o-xylene, chlorobenzene and the like or from the chloro solvents, preferably methylene chloride to provide triphenyl[2-cyclopropyl-4-(4-fluorophenyl)-quinoline-3-yl-methyl)-phosphonium]bromide salt compound of formula-2 which is purified in a suitable solvent selected from hydrocarbon solvents like benzene, toluene, xylene, and cyclohexane preferably toluene.

The fourth aspect of the present invention provides a novel crystalline form of (4R,6S)-(E)-6-{2-(2-cyclopropyl-4-(4-fluorophenyl)quinolin-3-yl]-vinyl]-2,2-dimethyl-[1,3]-dioxan-4-yl}-acetic acid tertiary butyl ester compound of formula-4.

The crystalline form of compound of formula-4 of the present invention is obtained by recrystallisation of compound of formula-4 from suitable alcoholic solvents, preferably methanol. The crystalline compound of formula-4 is characterized by its powder x-ray diffractogram having the peaks at 7.89, 9.98, 11.53, 14.87, 15.96, 17.51, 18.17, 19.18, 19.99, 20.86, 24.76 and 27.68±0.2 degrees of 2θ values (as illustrated in FIG. 1a), its IR spectrum having peaks at 3061, 2991, 2976, 1721, 1601, 1488 and 1197 cm$^{-1}$ and its DSC thermo gram having endothermic peak at about 114.59° C.

The fifth aspect of the present invention provides a novel crystalline form of pitavastatin tertiary butyl ester compound of formula-5.

Figure 1B:
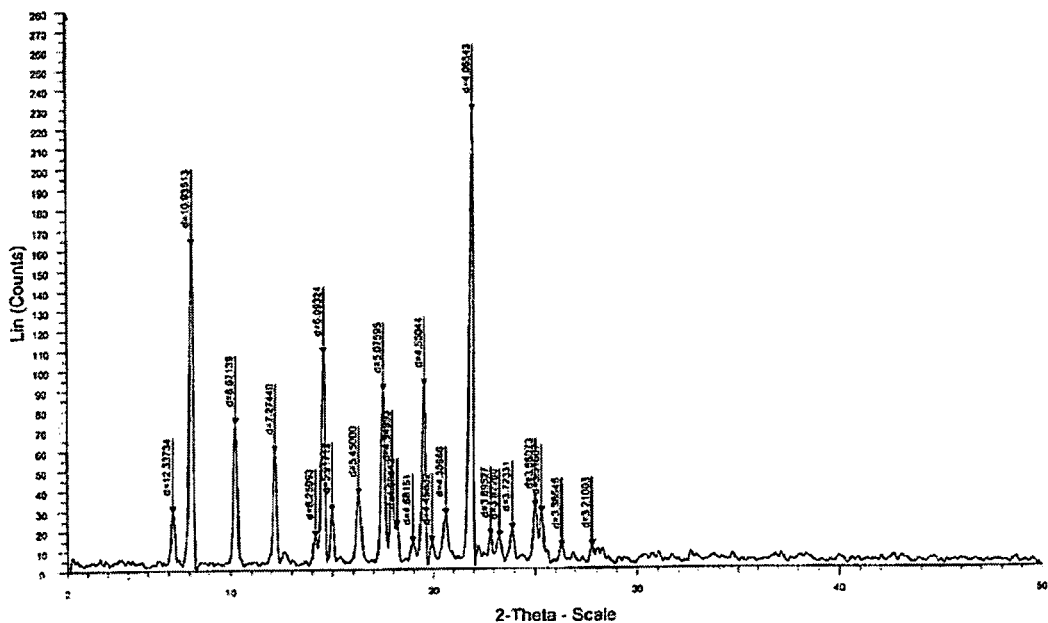
FIG. 1b: Illustrates the Powder X-ray diffraction pattern of pitavastatin tertiary butyl ester compound of formula-5.

The novel crystalline form of pitavastatin tertiary butyl ester compound of formula-5 of the present invention is obtained by recrystallisation of compound of formula-5 from a suitable solvent selected from hydrocarbon solvent, preferably toluene. This crystalline compound of formula-5 is characterized by its powder x-ray diffractogram peaks at 8.07, 10.19, 12.15, 14.52, 16.25, 17.45, 17.90, 19.49, 21.84 and 25.3±0.2 degrees of 2θ values (as illustrated in FIG. 1b), its IR spectrum having peaks at 3413, 3005, 2971, 1733, 1604, 1512, 1489, 1152 and 766 cm$^{-1}$ and its DSC thermo gram having endothermic peak at about 121.78° C.

The sixth aspect of the present invention is to provide crystalline form of pitavastatin methyl amine salt compound of formula-6a.

Formula -6a

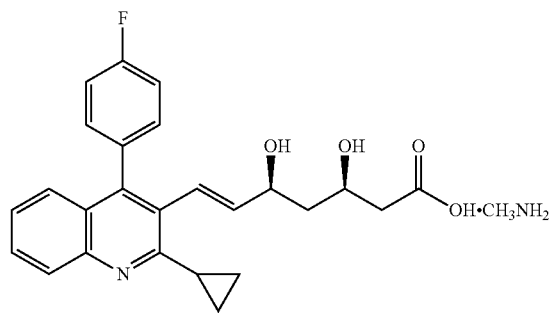

Figure 2A:
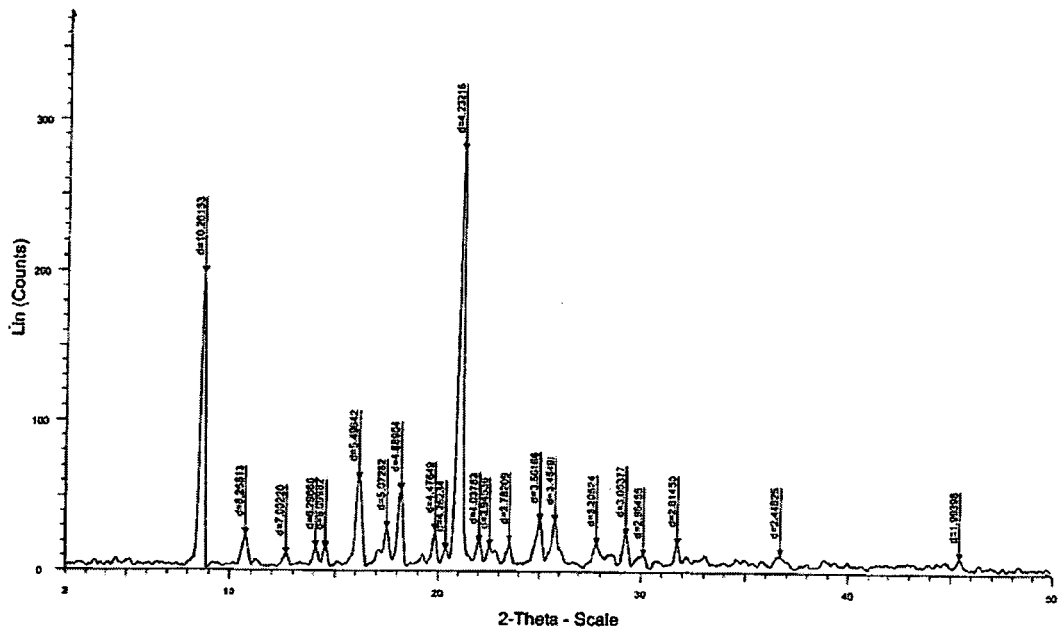
FIG. 2a: Illustrates the Powder X-ray diffraction pattern of pitavastatin methyl amine salt compound of formula-6a FIG. 2b: Illustrates the Powder X-ray diffraction pattern of pitavastatin free acid compound of formula-1a FIG. 3a: Illustrates the Powder X-ray diffraction pattern of pitavastatin sodium compound of formula-1b

The crystalline pitavastatin methylamine compound of formula-6a of the present invention is characterized by its powder x-ray diffractogram having the peaks at 8.61, 10.69, 16.11, 17.46, 18.13, 19.81, 20.97, 24.98, 25.76, 29.22 and 36.7±0.2 degrees of 2θ values (as illustrated in FIG. 2a), its IR spectrum having peaks at 3423, 3085, 3004, 2937, 1627, 1601, 1489, 1271, 1121 and 763 cm$^{-1}$ and its DSC thermo gram having endothermic peak at about 151.16° C.

The seventh aspect of the present invention is to provide a novel crystalline form of pitavastatin free acid compound of formula-1a.

The crystalline free acid of pitavastatin compound of formula-1a was obtained by hydrolyzing the pitavastatin tertiary butyl ester compound of formula-5 with a suitable alkali metal base in a suitable alcoholic solvent, preferably methanol to provide corresponding metal salt of pitavastatin, which on subsequent treatment with a suitable acid provides crystalline pitavastatin free acid, compound of formula-1a.

Formula -1a

Figure 2B:
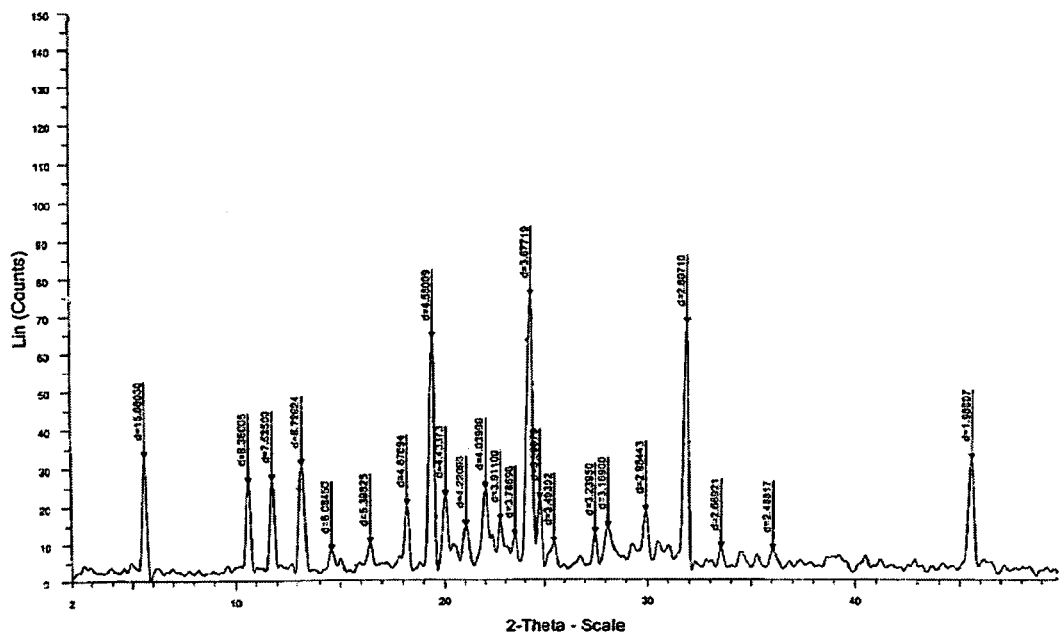

The crystalline pitavastatin free acid compound of formula-1a of the present invention is characterized by its powder x-ray diffractogram having the peaks at 5.56, 10.57, 11.73, 13.15, 18.17, 19.36, 20.01, 21.98, 24.18, 24.73, 31.85 and 45.59±0.2 degrees of 2θ values (as illustrated in FIG. 2b).

The eighth aspect of the present invention provides a crystalline form of pitavastatin sodium salt, compound of formula-1b.

Formula -1b

The crystalline form of pitavastatin sodium is obtained by treating the pitavastatin tertiary butyl ester compound of formula-1b with sodium hydroxide in a suitable alcoholic solvent.

Figure 3A:
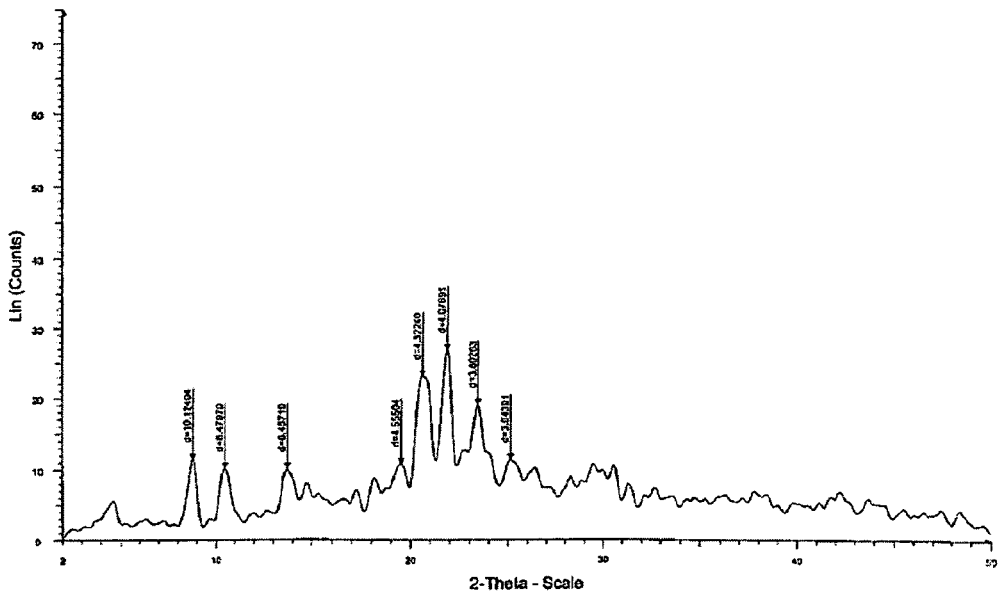
FIG. 3b: Illustrates the Powder X-ray diffraction pattern of prior art crystalline form of Pitavastatin calcium compound of formula-1c having water content 11.6.

The crystalline pitavastatin sodium compound of formula-1b of the present invention is characterized by its powder x-ray diffractogram having peaks at 8.72, 10.42, 13.70, 19.47, 20.53, 21.78, 23.37 and 25.10±0.2 degrees of 2θ values (as illustrated in FIG. 3a).

Figure 4A:
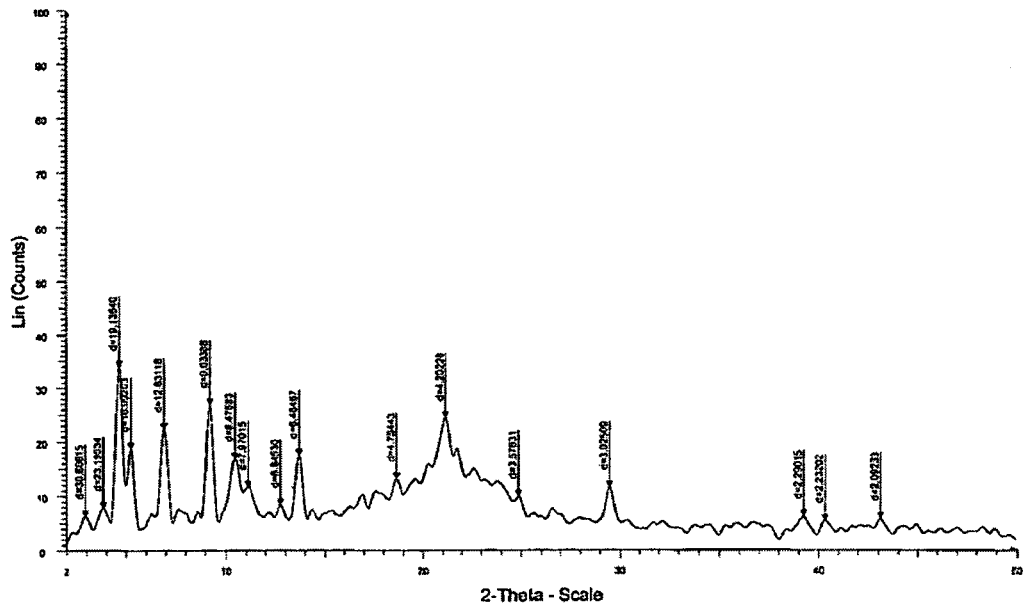
FIG. 4a: Illustrates the Powder X-ray diffraction pattern of prior art crystalline form of Pitavastatin calcium compound of formula-1c having water content 8.2.
Figure 4B:
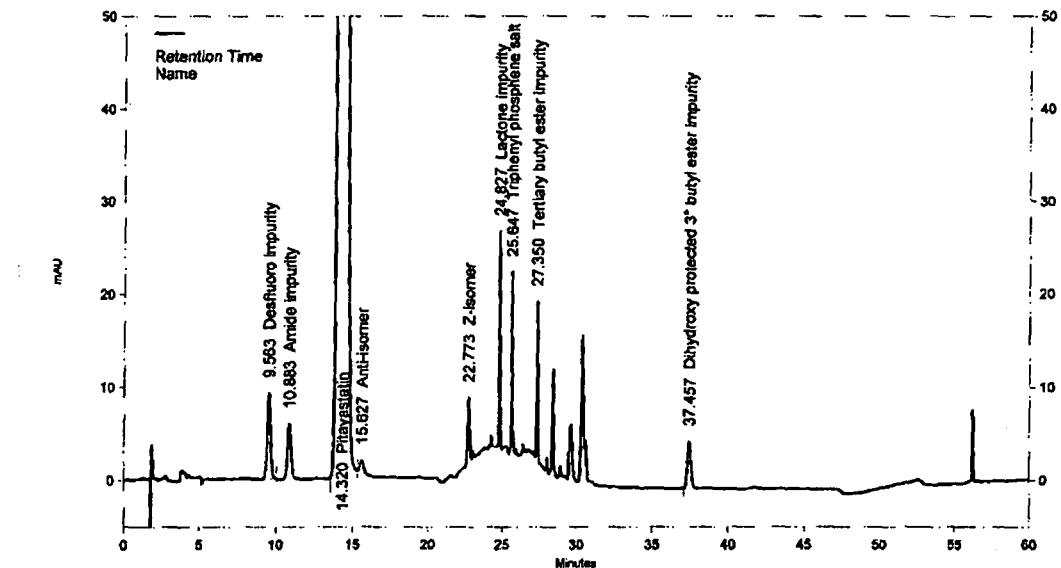
FIG. 4b: SST resolution chromatogram

We have prepared pitavastatin calcium as per example-2 of EP 0520406 B1, which involves the isolation of pitavastatin calcium from water and the obtained pitavastatin calcium is analyzed by PXRD. The powder X-ray diffractogram of the obtained crystalline pitavastatin calcium is illustrated in FIG. 4a.

Figure 3B:
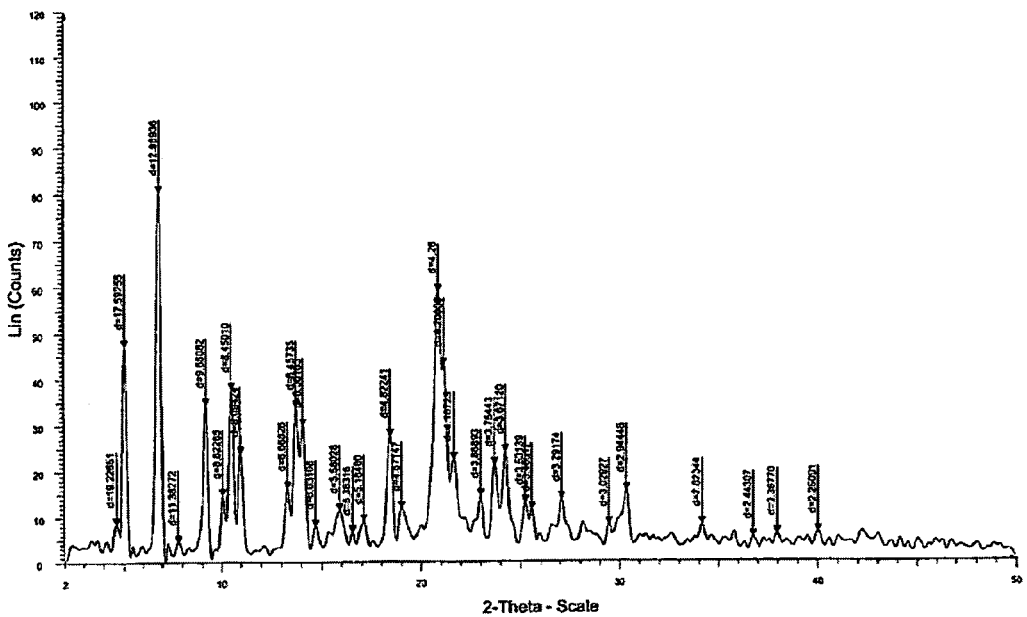

Similarly, we have isolated the pitavastatin calcium from water and analyzed the obtained solid by PXRD. The powder X-ray diffractogram of thus obtained crystalline pitavastatin calcium is illustrated in FIG. 3b. Hence both the crystalline forms of pitavastatin calcium illustrated in FIG. 3b and FIG. 4a are prior art crystalline forms. The impurities A to D are shown in the following table with structural formula:

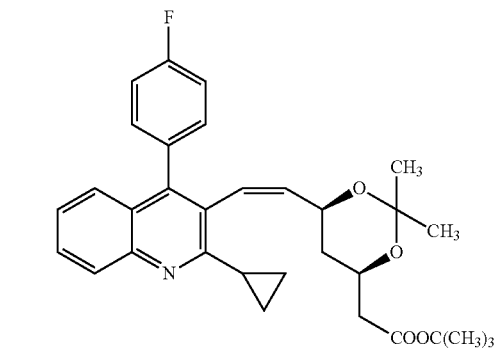

Impurity-A

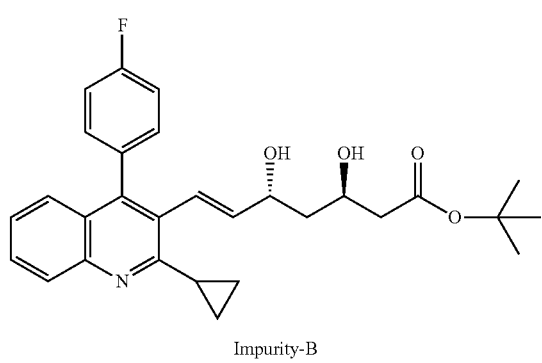 [SMILES: CC(C)(C)OC(=O)C[C@H](O)C[C@@H](O)/C=C/c1c(C2CC2)nc2ccccc2c1-c1ccc(F)cc1]

Impurity-B

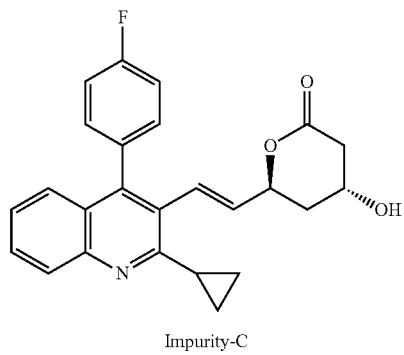 [SMILES: O=C1C[C@H](O)C[C@@H](/C=C/c2c(C3CC3)nc3ccccc3c2-c2ccc(F)cc2)O1]

Impurity-C

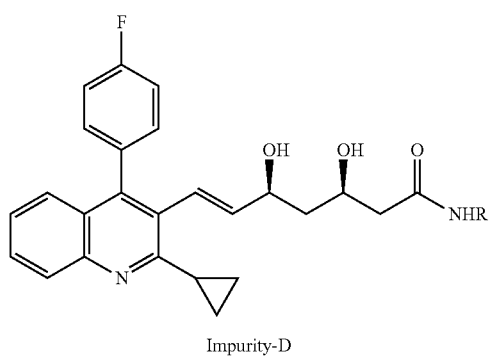

Impurity-D

Other than the above impurities, the following impurities (3R,5R,6E)-7-[2-cyclopropyl-4-(4-Fluorophenyl)quinolin-3-yl]-3,5-dihydroxy-6-heptenoic acid calcium (herein designated as Impurity-E), racemic pitavastatin calcium (herein designated as impurity-F), Monocalcium bis[(3R,5S,6Z)-7-[2-cyclopropyl-4-(4-fluorophenyl)-3-quinolinyl]-3,5-dihydroxy-6-heptenoate (herein designated as Impurity-G), (3R, 5S, 6E)-7-[2-cyclopropyl-4-(phenyl)quinolin-3-yl]-3,5-dihydroxy-6-heptenoic acid calcium salt (herein designated as Impurity-H), (3R,5S,E)-tert-butyl 7-(2-cyclopropyl-4-(4-fluorophenyl)-quinolin-3-yl)-3,5-dihydroxyhept-6-enoate (herein designated as Impurity-I) and (3R,5S,6E)-methyl-7-(2-cyclopropyl-4-(4-fluorophenyl)quinolin-3-yl)-3,5-dihydroxyhept-6-enoate (herein designated as Impurity-J). All the above impurities are identified and well characterized. The structures of the impurities are represented as follows.

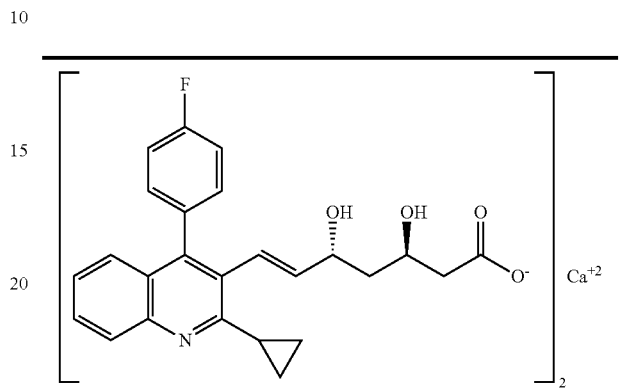

Impurity-E

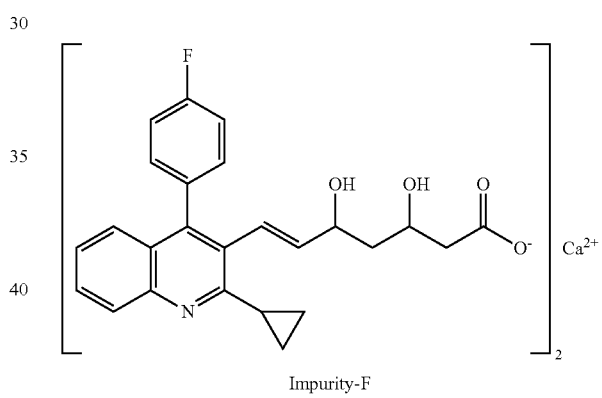

Impurity-F

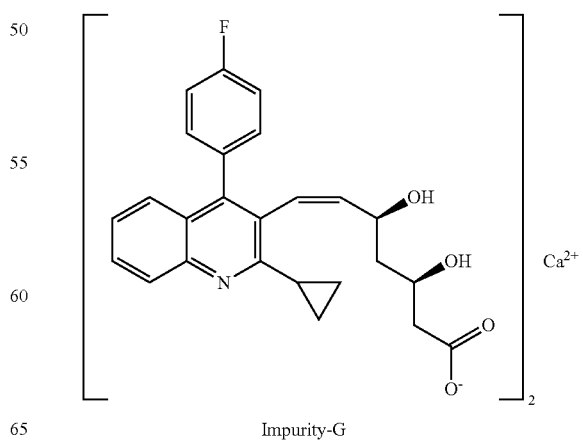

Impurity-G

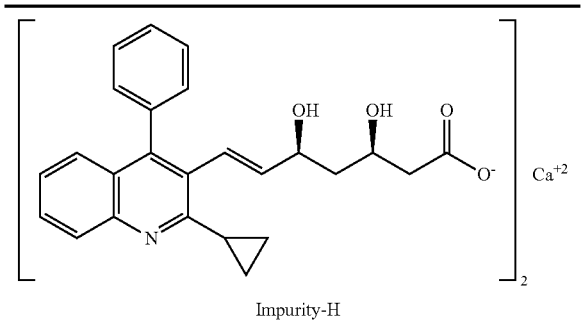
Impurity-H
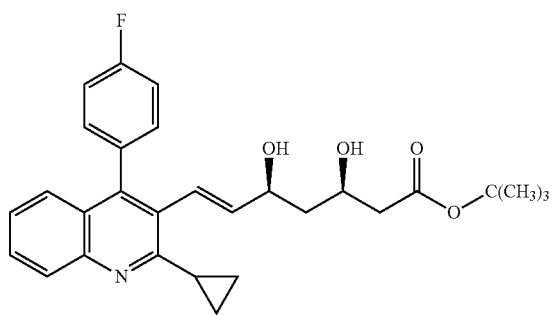
Impurity-I
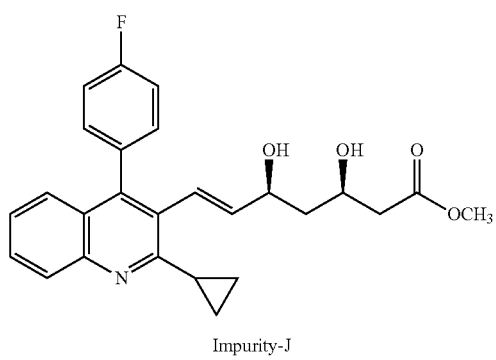 [SMILES: COC(=O)C[C@H](O)C[C@H](O)/C=C/c1c(C2CC2)nc2ccccc2c1-c1ccc(F)cc1]
Impurity-J
Other than the above discussed impurities, the impurities with the following structural formulas also observed in the synthesis of pitavastatin calcium.
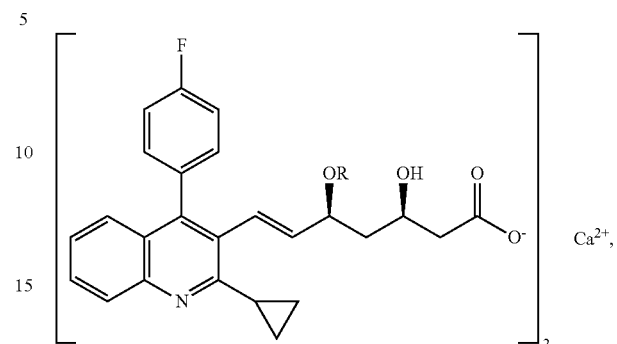
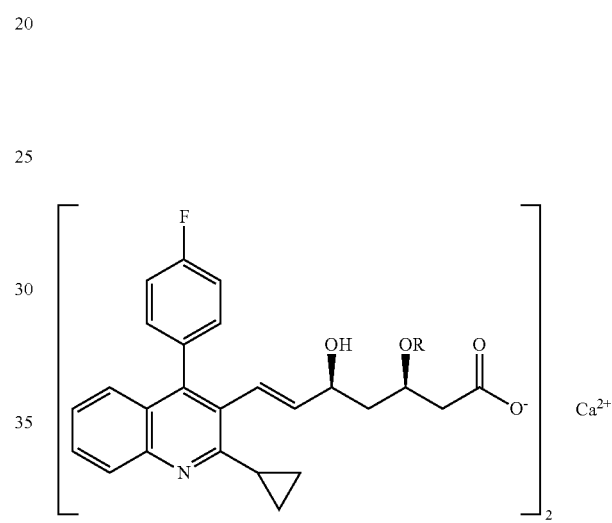
wherein R is alkyl
The present invention is schematically represented as follows:

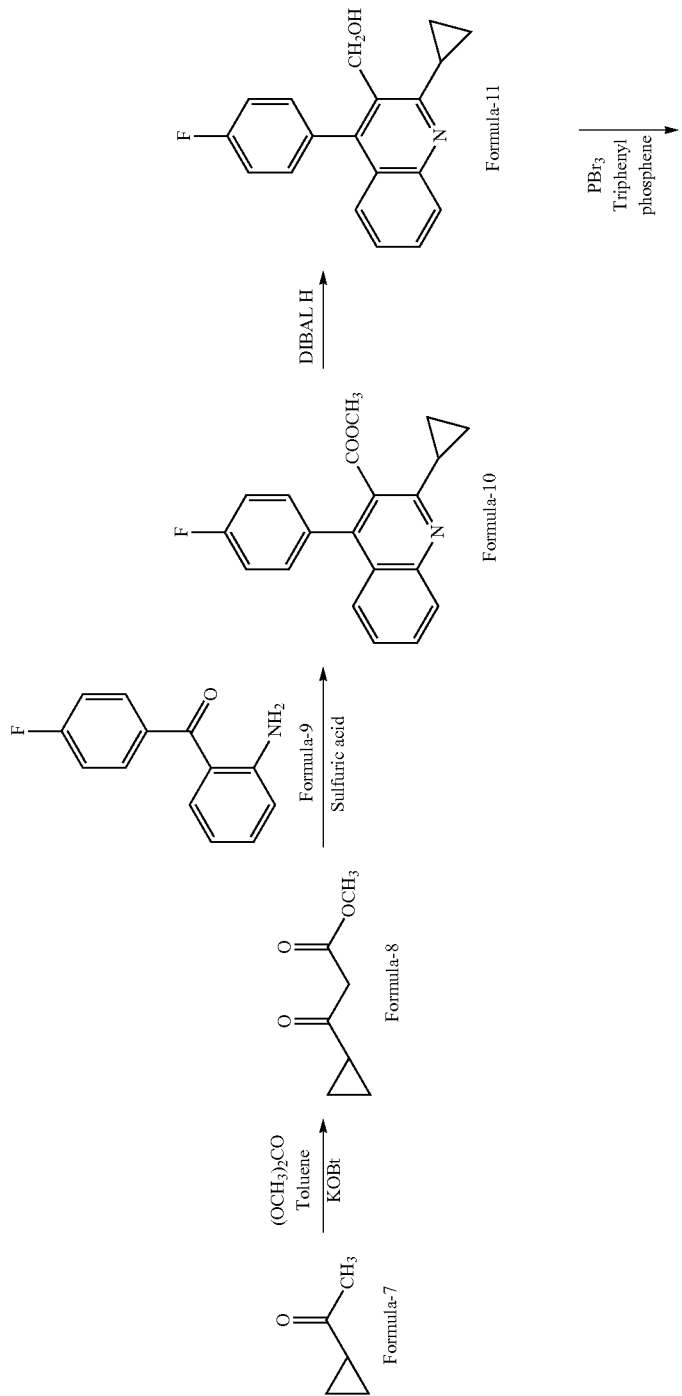

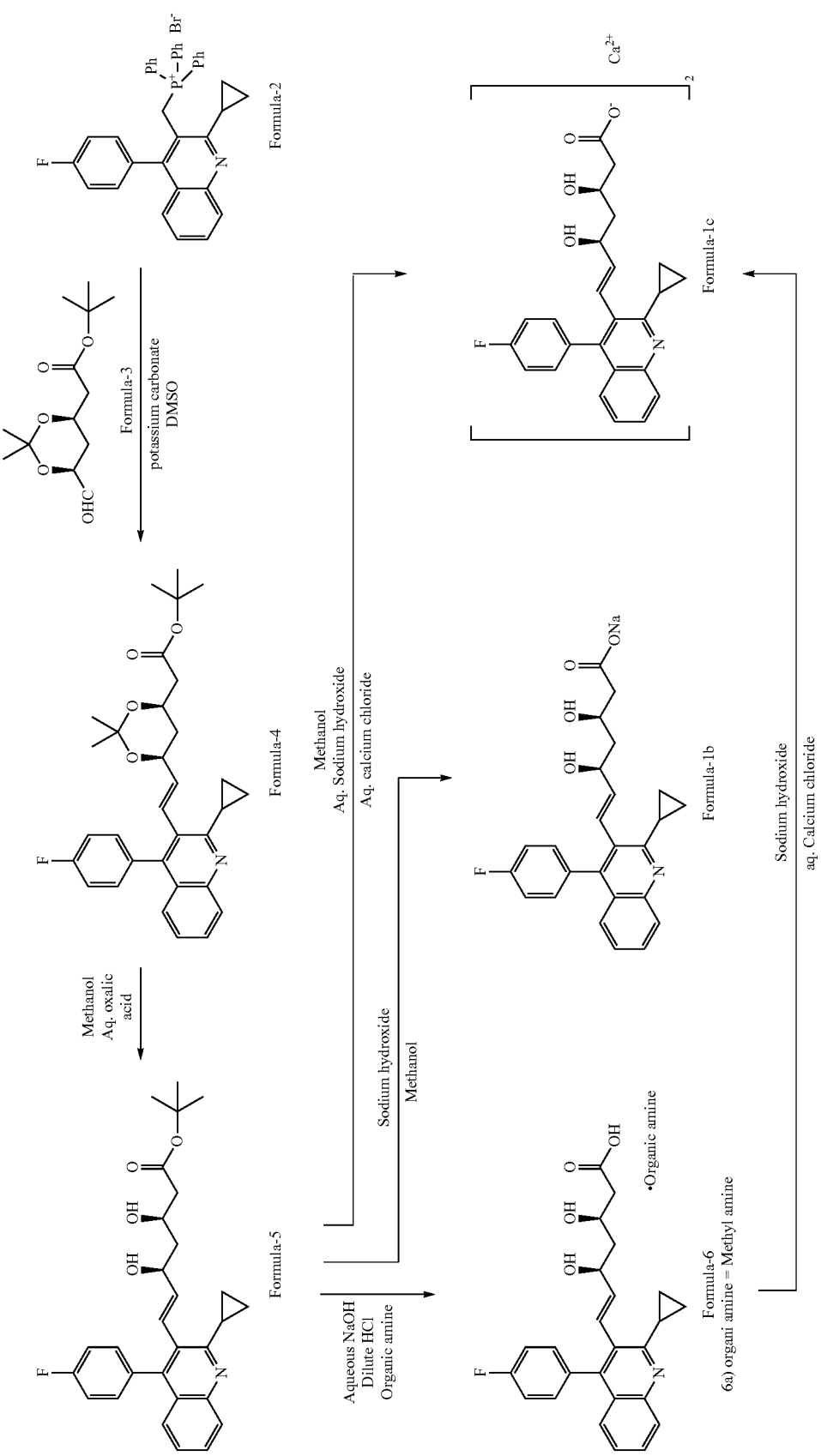

XRD analysis of pitavastatin, its pharmaceutically acceptable salts as well as their intermediates were carried out using SIEMENS/D-5000 X-Ray diffractometer using Cu, Ka radiation of wavelength 1.54 A° and continuous scan speed of 0.045°/min. FI-IR spectrum of pitavastatin, its pharmaceutically acceptable salts as well as their intermediates were recorded on Thermo model Nicolet-380 as KBr pellet. The thermal analysis of pitavastatin, its pharmaceutically acceptable salts as well as their intermediates were carried out on Waters DSC Q-10 model differential scanning calorimeter.

Related substances and photo (UV) degradation impurities of the pitavastatin calcium are measured by HPLC, as per the following conditions.
Apparatus: A liquid chromatograph is equipped with variable wavelength UV-detector.
Column: ACE C18 250×4.0 mm, 5 µm; Flow rate: 1.2 ml/min; Wavelength: 250 nm; Temperature: 50° C.; Injection volume 20 µL; Run time 60 min; Product retention time: 14.0 minutes; using water:acetonitrile as a diluent; Elution: gradient;

| Impurity | RRT |
| --- | --- |
| Impurity-C (Lactone) | 1.73 |
| Impurity-D (Amide) | 0.759 |
| Impurity-E (Antiisomer) | 1.09 |
| Impurity-G (Z-isomer) | 1.59 |
| Impurity-H (Desfluoro) | 0.67 |
| Impurity-I (Tertiary butyl ester) | 1.91 |
| Triphenyl phosphene salt | 1.79 |
| Dihydroxy protected tertiary butyl ester(Formula-4) | 2.62 |

Pitavastatin calcium or its pharmaceutically acceptable salts prepared as per the present invention is further micronized or milled to get the desired particle size. The novel crystalline compound of formula-4,5,6a and 1a of the present invention used to prepare highly pure pitavastatin and its pharmaceutically acceptable salts i.e., having purity greater than 99.00%, preferably >99.50% by HPLC and 99.95% by HPLC.

The pitavastatin calcium particles prepared as per the present invention having mean particle size in the range of 2 to 70 microns and $D_{90}$ particles in the range of 2 to 100 microns. The particle size distribution of pitavastatin calcium was analyzed by the conventional methods.

The process described in the present invention was demonstrated in examples illustrated below. These examples are provided as illustration only and therefore should not be construed as limitation of the scope of the invention.

EXAMPLES

Example-1

Preparation of Methyl 3-cyclopropyl-3-oxopropanoate

To the solution of dimethyl carbonate (361 g) in toluene (1250 ml) added cyclopropyl methyl ketone (125 g) and stirred for 15 min at 25° C. Cooled the reaction mixture to 10° C., added potassium tert.butoxide (100 g) to it under nitrogen atmosphere. Heated the reaction mixture to 75° C. and stirred for 14 hrs. Cooled the reaction mixture to 25° C. and slowly poured it into chilled water (750 ml). Cooled the reaction mixture to 0° C. and adjusted the pH to 2.5 by using 50% HCl solution. Raised the temperature to 25° C. and stirred for 45 minutes. Separated the both organic and aqueous layers. Extracted the aqueous layer with toluene (500 ml). Washed the organic layer with water (500 ml). Distilled off the toluene completely from organic layer under reduced pressure to get the title compound.
Yield: 130 g; G.C. purity: 93.85%

Example-2

Preparation of methyl 2-cyclopropyl-4-(4-fluorophenyl)quinoline-3-carboxylate

To the solution of 2-amino-4'-fluorobenzophenone (100 g) in methanol (500 ml) added Methyl 3-cyclopropyl-3-oxopropanoate (132 g), sulfuric acid (5 ml) and stirred for 15 minutes at 25° C. Heated the reaction mixture to 65° C. for 22 hrs. Distilled off the methanol completely under reduced pressure. Cooled the reaction mixture to 25° C., added water (500 ml) and stirred for 30 minutes. Cooled the reaction mixture to 0° C. and pH adjusted to 6.0 with sodium carbonate solution. Stirred the reaction mixture for 45 minutes at 25° C. Filtered the cake and washed with water. Spin dry the compound for 60 minutes. To this compound added methanol (150 ml) and stirred for 1 hr at 25° C. Filtered the solid and washed with methanol (50 ml). Dried the obtained solid to get the title compound.
Yield: 141.6 g; MR: 123-125° C.;
Purity by HPLC: 99.69%

Example-3

Preparation of methyl 2-cyclopropyl-4-(4-fluorophenyl)quinoline-3-carboxylate

To the solution of 2-amino-4'-fluorobenzophenone (100 g) in acetic acid (500 ml) added methyl 3-cyclopropyl-3-oxopropanoate (132 g), sulfuric acid (5 ml) and stirred for 15 minutes at 25° C. Heated the reaction mixture to 100° C. for 10 hrs. Cooled the reaction mixture to 0-5° C. and pH adjusted to neutral conditions with 40% sodium hydroxide solution. Filtered the solid formed and washed with water. The wet solid was dissolved in methylene chloride and separated the water from it. Silica slurry was given to the reaction mixture and filtered it. Methylene chloride was distilled off and the compound was co-distilled with methanol. To the compound added methanol (150 ml) and stirred for 1 hr at 25° C. Filtered the solid and washed with methanol (50 ml). Dried the obtained solid to get the title compound.
Yield: 101 g.

Example-4

Preparation of methyl 2-cyclopropyl-4-(4-fluorophenyl)quinoline-3-carboxylate

The title compound is prepared analogous manner to example-3 using p-toluene sulfonic acid in place of sulfuric acid.
Yield: 100.5 g.

Example-5

Preparation of (2-cyclopropyl-4-(4-fluorophenyl) quinoline-3-yl)methanol

To 50 g of methyl 2-cyclopropyl-4-(4-fluorophenyl)quinoline-3-carboxylate added toluene (250 ml) and stirred for 15 minutes at 25° C. Cooled the reaction mixture to 0° C. Added 300 ml of DIBAL H (25% solution in toluene) to the reaction mixture slowly in 45 minutes at the same temperature. Stirred the reaction mixture for 1 hr at 0° C. Quenched the reaction mixture with HCl (110 ml) solution at 10° C. and stirred for 15 minutes. Raised the temperature to 25° C. and stirred for 30 minutes. Separated the both aqueous and organic layers. Extracted the aqueous layer with toluene (400 ml). Adjusted the pH of the reaction mixture with 10% sodium bicarbonate solution (200 ml). Washed the organic layer with saturated sodium chloride solution (200 ml). Distilled off the solvent completely to obtain a solid. Added cyclohexane (50 ml) to the solid and distilled it. To the residue added cyclohexane (150 ml) and stir for 30 minutes at 45° C. Cooled the reaction mixture to 25° C. and stirred for 1 hr. at the same temperature. Filtered the cake, washed with cyclohexane (50 ml) and then dried to get the title compound.

Yield: 44 g.; MR: 125-135° C.; Purity by HPLC: 99.83%; Des-fluoro: 0.12%

Example-6

Preparation of triphenyl (2-cyclopropyl-4-(4-fluorophenyl)quinoline-3-yl)-phosphonium bromide To 100 g of (2-cyclopropyl-4-(4-fluorophenyl)quinoline-3-yl)methanol added dichloromethane (400 ml). Stirred the reaction mixture for 30 minutes. To this reaction mixture added a solution of phosphorous tribromide (16.2 ml) in dichloromethane (100 ml) slowly at 25° C. and stirred for 1 hr at same temperature. Quenched the reaction mixture with 10% sodium bicarbonate solution and adjusted the pH to neutral at 20° C. Stirred the reaction mixture to 15 minutes. Separated the both aqueous and organic layers. Extracted the aqueous layer with dichloromethane (100 ml). Washed the organic layer with 10% hypo solution. Then again washed the organic layer with saturated sodium chloride solution. Heated the reaction mixture to 40° C. To the reaction mixture added triphenyl phosphene (90 g) in dichloromethane (100 ml) and stirred. Distilled off the solvent completely under reduced pressure. Added toluene (100 ml) to the reaction mixture and stirred for 15 minutes. Distilled off the toluene completely. Cooled the reaction mixture to 40° C., added toluene (500 ml) and heated for 1 hr at 75° C. Cooled the reaction mixture to 25° C. and stirred for 1 hr. Filtered the reaction mixture and washed the compound with toluene and dried. The compound obtained as a crystalline solid.

Yield: 200 g. MR: 215-218° C.; Purity by HPLC: 99.61%, desfluoro-0.08%;

Example-7

Preparation of triphenyl (2-cyclopropyl-4-(4-fluorophenyl)quinoline-3-yl)-phosphonium bromide (One pot process)

To 50 g of methyl 2-cyclopropyl-4-(4-fluorophenyl)quinoline-3-carboxylate added toluene (500 ml) and stirred for 15 minutes at 25° C. Added 145 ml of vitride (65% solution in toluene) to the reaction mixture slowly in 45 minutes at the same temperature under nitrogen atmosphere. Stirred the reaction mixture for 4 hrs at 25° C. Quenched the reaction mixture with hydrochloric acid (55 ml) solution and stirred for 30 minutes. Separated the both aqueous and organic layers. Extracted the aqueous layer with ethyl acetate. Neutralized the reaction mixture with 10% sodium bicarbonate solution. Washed the organic layer with saturated sodium chloride solution. Distilled the solvent completely under reduced pressure. To the above obtained compound, 250 ml of dichloromethane was added. To this reaction mixture phosphorous tri bromide was slowly added and stirred for 3 hrs. Adjusted the pH with 10% sodium bicarbonate solution. Separated the both aqueous and organic layers. Aqueous layer was extracted with dichloromethane and washed with hypo solution. Again the reaction mixture was washed with sodium chloride solution. Heated the reaction mixture to 40° C. To this added a solution of triphenyl phosphene (38.4 g) in dichloromethane (50 ml). Stirred the reaction mixture for 2 hrs. Distilled off the solvent completely under reduced pressure. To this added 250 ml of toluene and stirred for 2 hrs. Filtered the solid precipitated and dried it. The title compound obtained as a crystalline solid.

Yield: 88 g.; M.R: 215-218° C.

Example-8

Preparation of (4R,6S)-(E)-6-{2-(2-cyclopropyl-4-(4-fluorophenyl)quinolin-3-yl)-vinyl]-2,2-dimethyl-[1,3]-dioxan-4-yl}-acetic acid tertiary butyl ester To the solution of triphenyl (2-cyclopropyl-4-(4-fluorophenyl)quinoline-3-yl)-phosphonium bromide (60 g) in DMSO (100 ml) added a solution of tert-butyl 2-((4R,6S)-6-formyl-2,2-dimethyl-1,3-dioxan-4-yl)acetate (25 g) in DMSO (50 ml). Heated the reaction mixture to 75° C. and added potassium carbonate (20 g) to it. Stirred the reaction mixture for 7 hrs at 75° C. Cooled the reaction mixture to 25° C., added water (250 ml) and stirred for 90 minutes at same temperature. Filter the solid precipitated and washed with water (200 ml). To the obtained wet solid added methanol (250 ml) and stirred for 45 minutes at 65° C. Cooled the reaction mixture to 25° C. and stirred for 90 minutes. Filtered the compound and washed with methanol (25 ml) and dried. The compound obtained as a crystalline solid.

Yield: 35 g.; M.R: 111-113° C.;
Purity by HPLC: 97.65%; Impurity-A: 0.40%, Impurity-J: 0.90%

Example-9

Preparation of pitavastatin tertiary butyl ester

To the solution of (4R,6S)-(E)-6-{2-(2-cyclopropyl-4-(4-fluorophenyl)quinolin-3-yl)-vinyl]-2,2-dimethyl-[1,3]-dioxan-4-yl-acetic acid tertiary butyl ester (150 g) in methanol (750 ml) added a solution of oxalic acid (90 g) in water (630 ml). Stirred the reaction mixture for 6 hrs at 35° C. Cooled the reaction mixture to 10° C. Adjusted the pH to 7.0 by using sodium carbonate solution (72 g in 360 ml of water). Stirred the reaction mixture for 45 minutes at 10° C. Heated the reaction mixture to 30° C. and stirred for 2 hrs. Filtered the solid and washed with water (100 ml). To the wet solid added water (2250 ml) and stirred for 2.5 hrs at 30° C. Filtered the reaction mixture and washed the solid with water (100 ml). To the wet solid added toluene (75 ml) and stirred for 30 minutes at 75° C. Cooled the reaction mixture to 0° C. and stirred for 3 hrs at same temperature. Filtered the solid and washed with cyclohexane (150 ml). Suck dried the compound for 1 hr. under reduced pressure. To this solid added toluene (75 ml) and stirred for 30 minutes at 75° C. Cooled the reaction mixture to 0° C. and stirred for 3 hrs at same temperature. Filtered the solid and washed with cyclohexane (150 ml) and dried the compound. Compound obtained as a crystalline solid.

Yield: 110 g.; M.R: 120-122° C.

Purity by HPLC: 99.67%; Impurity-C, 0.05%, des-fluoro: 0.08%; Impurity-J: 0.04%

Example-10

Preparation of Pitavastatin Tert Butyl Ester (with HCl)

The title compound is prepared analogous manner to example-3 using hydrochloric acid for deprotection in place of oxalic acid.
Yield: 105 g.

Example-11

Preparation of Pitavastatin Methyl Amine Salt 150 g of pitavastatin tert butyl ester was dissolved in acetonitrile (1500 ml). To this solution added sodium hydroxide solution (45 g in 450 ml of water) at 30° C. slowly and stirred the reaction mixture for 1.5 hrs at same temperature. Cooled the reaction mixture to 0° C. and added sodium chloride (280 g) to it. Adjusted the pH to 4.0 with 10% HCl solution (60 ml in 600 ml of water). Stirred the reaction mixture for 15 minutes and separated the both aqueous and organic layers at 0° C. To the organic layer methyl amine (36 ml) was added at 0° C. and stirred for 30 minutes. Stirred for another 30 minutes at 30° C. Distilled off the solvent completely under reduced pressure. To the reaction mixture added acetonitrile (150 ml) and distilled off completely. To the reaction mixture added acetonitrile (750 ml) and stirred for 1 hr at 30° C. Cooled the reaction mixture to 0° C. and stirred for 1.5 hrs at same temperature. Filtered the reaction mixture and washed with chilled acetonitrile (150 ml) and dried it. The compound obtained as a crystalline solid. Yield: 110 g; M.R: 146-149° C.

Example-12

Preparation of Pitavastatin Free Acid

From pitavastatin calcium salt: 20 g of pitavastatin calcium salt was taken in 100 ml of dichloro methane and stirred for 10 minutes. Cooled the reaction mixture to 0° C. and adjusted the pH to 3.0 with 20% aqueous HCl solution. 60 g of sodium chloride is added to the reaction mixture and stirred for 10 minutes. Raised the temperature to 25° C. and stirred for 30 minutes. Filtered the solid precipitated. Water was added to the solid and stirred for 10 minutes. Filtered the solid and washed with water. Dried the obtained solid to get the title compound.
Yield: 17 g; M.R: 125-130° C.
From pitavastatin tertiary butyl ester: 50 g of pitavastatin tert-butyl ester was taken in 250 ml of methanol and stirred for 10 minutes at 25° C. 6 g of sodium hydroxide is dissolved in 60 ml of water and slowly added to the reaction mixture. Stirred the reaction mixture to 2 hrs at 25°. Distilled off the solvent completely under reduced pressure. To the obtained solid added 50 ml of dichloro methane and stirred for 10 minutes. Cooled the reaction mixture to 0° C. and adjusted the pH to 3.0 with 20% aqueous HCl solution. 60 g of sodium chloride is added to the reaction mixture and stirred for 15 minutes. Raised the temperature to 25° C. and stirred for 30 minutes. Filtered the solid precipitated. Water was added to the solid and stirred for 10 minutes. Filtered the solid and washed with water. Dried the obtained solid to get the title compound.
Yield: 42 g; M.R: 125-130° C.

Example-13

Preparation of Pitavastatin Sodium Salt 10 g of pitavastatin tert-butyl ester was taken in 100 ml of methanol and stirred for 10 minutes at 25° C. 3 g of sodium hydroxide is dissolved in 30 ml of water and slowly added to the reaction mixture. Stirred the reaction mixture to 2 hrs at 25°. Distilled off the solvent completely under reduced pressure. The obtained solid was washed with water and dried the compound. The title compound obtained as a crystalline solid.
Yield: 7 g.; M.R: 100-110° C.

Example-14

Preparation of Pitavastatin Calcium Salt 20 g of pitavastatin methyl amine salt was dissolved in water (120 ml). To this solution added sodium hydroxide solution (1.76 g in 20 ml water) and stirred for 45 minutes at 30° C. Tert butyl acetate (40 ml) was added to the reaction mixture and stirred for 15 minutes. Separated the tert butyl acetate from the reaction mixture. Removed the methyl amine and tert butyl acetate traces with nitrogen expelling upto the pH reaches to 9.0. Filtered the reaction mixture and washed with water (20 ml). Calcium chloride (3.9 g) was dissolved in water (20 ml) and added to the reaction mixture at 35° C. and stirred for 45 minutes at same temperature. Filtered the solid and dried the crystals.
Yield: 15 g.; MR: 206-209° C.

Example-15

Preparation of Pitavastatin Calcium Salt 10 g of pitavastatin tert-butyl ester compound was dissolved in 50 ml of methanol and stirred for 10 minutes. Cooled the reaction mixture to 0° C. and added aqueous sodium hydroxide solution (3 g of NaOH in 30 ml of water) slowly to it at the same temperature. Stirred the reaction mixture for 90 minutes at 0° C. Distilled off the solvent completely from reaction mixture. To the obtained residue added water (60 ml) and stirred for 15 minutes. The pH of the reaction mixture was adjusted to 9.0 by using 10% HCl solution at 10° C. Heated the reaction mixture to 30° C. and washed it by using tert-butyl acetate. Added 160 ml of water to the reaction mixture and adjusted the pH to 9.0 by using 10% NaOH solution. Then treated the reaction mixture with aqueous calcium chloride solution (1.92 g of $CaCl_2$ in 100 ml of water). Stirred the reaction mixture for 40 minutes at 25° C. Then cooled the reaction mixture to 10°-15° C. and stirred overnight at the same temperature. Filtered the solid precipitated, washed with water and dried the compound. The compound obtained as a crystalline solid. The powder X-ray diffractogram of the above obtained compound is perfectly matched with the prior art crystalline form of pitavastatin calcium.
Yield: 9.2 g.; Water content: 11.6%
Purity by HPLC: 99.75%; Impurity-H: 0.09%; Impurity-E: 0.06%; Impurity-C: 0.02%
Particle Size Distribution (PSD): D(0.1) is 1.45 µm; D(0.5) is 5.23 µm; D(0.9) is 12.08 µm; D[4.3] is 6.10 µm.

Example-16

Preparation of Prior Art Crystalline Form of Pitavastatin Calcium as Per the Example 2 of EP 0520406B1

To a 12 g of (E)-3(R)-5(S)-dihydroxy-7-[4'-(4"-fluorophenyl)-2'-cyclopropyl quinoline-3'-yl]hept-6-ene acid D(+) phenyl ethylamine salt compound((−)I (+)II), 24.3 ml of a 1N sodium hydroxide aqueous solution and 200 ml of water were added and stirred to dissolve the compound. To this solution an aqueous calcium chloride solution obtained by dissolving 1.47 g of dry calcium chloride to 200 ml of water, was dropwise added. This reaction solution was stirred overnight, and the resulting white precipitate was collected by filtration to obtain 9.0 g of white crystals.

MR: 190-192° C. (decomposed); Water content: 8.2%

Example-17

Preparation of Pitavastatin Calcium Salt 10 g of pitavastatin tert-butyl ester compound was dissolved in 50 ml of isopropyl alcohol and stirred for 60 minutes at 25-30° C. Cooled the reaction mixture to 0-10° C. and added aqueous sodium hydroxide solution (3 g of NaOH in 30 ml of water) slowly to it at the same temperature. Stirred the reaction mixture for 90 minutes at 0-10° C. Distilled off the solvent completely from reaction mixture. Water (60 ml) was added to the obtained residue and stirred for 15 minutes. The pH of the reaction mixture was adjusted to 9.2 by using 10% HCl solution at 10° C. Heated the reaction mixture to 30° C. and washed it with tert-butyl acetate. Added 160 ml of water to the reaction mixture and adjusted the pH to 9.2 by using 10% NaOH solution. Then treated the reaction mixture with aqueous calcium chloride solution (1.92 g of $CaCl_2$ in 100 ml of water) at 35-40° C. for 1.5 hours and stirred for 3 hours. Filtered the precipitated solid and washed with water. The wet solid was suspended in water and stirred for 10 hours at 35-45° C. The solid was filtered, washed with and dried to get the title compound. Yield: 9 g. μ; PSD: D(0.1) is 0.89 μm; D(0.5) is 3.02 μm; D(0.9) is 7.04 μm; D[4.3] is 3.54 μm.

Example-18

UV Degradation Study of Pitavastatin Calcium 0.1 g of pitavastatin calcium salt was dissolved in 100 ml of water and acetonitrile mixture and irradiated with UV light (130 W, 30° C.) for 48 hrs. Acetonitrile and water were evaporated under vacuum. The two photo degradants (compound A and B) of pitavastatin are obtained. Compound A (RRT: 0.281) & Compound B (RRT: 1.543)

What is claimed is:

1. A process for the preparation of a compound of Formula-1,

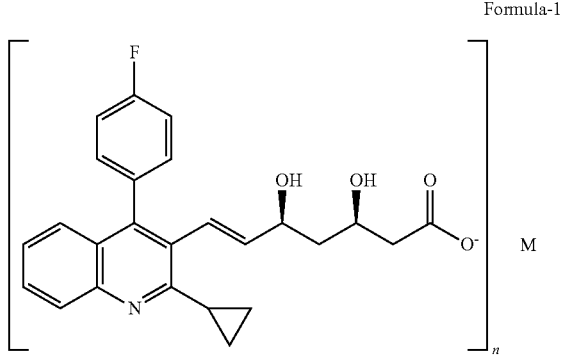

Formula-1 wherein M is $H^+$, $Na^+$ or $K^+$ and n is 1 or M is $Mg^{+2}$ or $Ca^{+2}$ and n is 2, comprising:

a) reacting a compound of Formula-2,

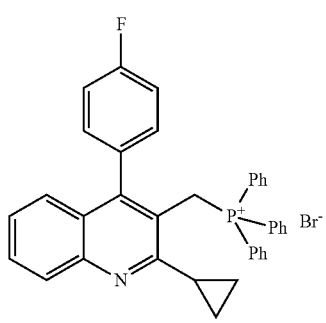

Formula-2 with a compound of Formula-3,

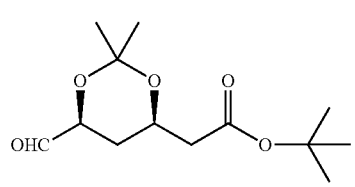

Formula-3 in the presence of a base in a solvent to obtain a compound of Formula-4,

Formula-4

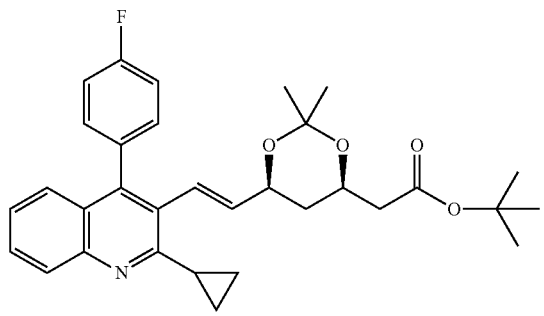

then recrystallizing the compound of Formula-4 from a second solvent, thereby removing Impurity A Impurity-A

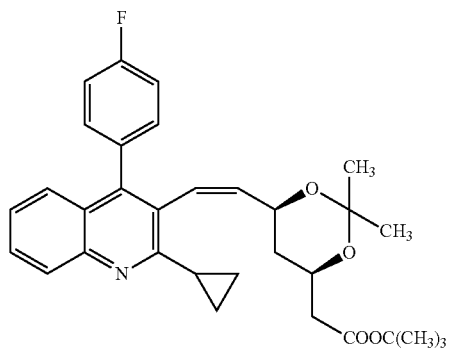

and obtaining the compound of Formula-4 as a crystalline solid;

b) reacting the recrystallized compound of Formula-4 with an acid in a solvent to obtain a compound of Formula-5, Formula-5

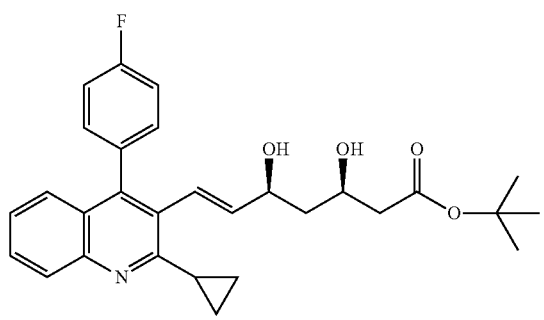

then recrystallizing the compound of Formula-5 from a hydrocarbon solvent, thereby removing Impurity B Impurity-B

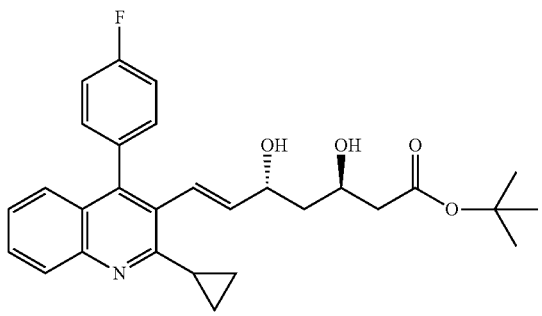

and obtaining the compound of Formula-5 as a crystalline solid;

c) hydrolyzing the recrystallized compound of Formula-5 in the presence of a base in a solvent to obtain a carboxylic acid, then treating the carboxylic acid with an organic amine to obtain a compound of Formula 6, Formula-6

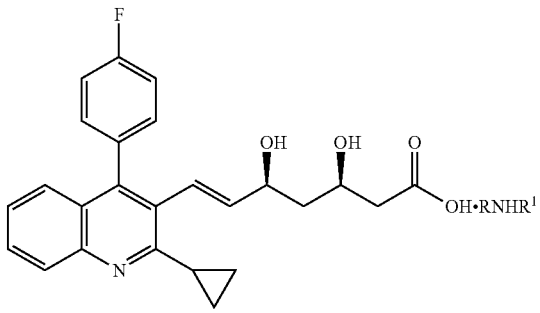

wherein R is alkyl, aryl, aralkyl or substituted aryl and $R^1$ is hydrogen, alkyl, aryl, aralkyl or substituted aryl, then recrystallizing the compound of Formula-6 from a second solvent; and d) treating the recrystallized compound of Formula-6 with a base in a solvent to obtain the compound of Formula-1.

2. The process according to claim 1, wherein step d) further comprises treating the compound of Formula-1 with a calcium source to obtain the compound of Formula-1 wherein M is $Ca^{2+}$ and n is 2.

3. The process of claim 2, wherein:
in step a), the base is an alkali metal carbonate and the solvent is a polar aprotic solvent;
in step b), the acid is hydrochloric acid, hydrobromic acid, acetic acid, sulfuric acid, oxalic acid, para toluene sulfonic acid, poly phospharic acid, methane sulphonic acid, maleic acid, malic acid, fumaric acid or formic acid and the solvent is an alcoholic solvent or a hydrocarbon solvent;
in step c), the base is selected from an alkali metal hydroxide, an alkali metal carbonate or an alkali metal bicarbonate; the solvent is a nitrile solvent; and the organic amine is methyl amine, ethyl amine, n-propyl amine, isopropyl amine, n-butyl amine, tertiary butyl, (+/−)-sec-butyl amine, octyl amine, 2-ethyl hexylamine, benzyl amine, α-methyl-benzylamine, phenyl ethylamine, dibenzylamine, N-methylbenzylamine, N,N -dimethylbenzylamine, N,N-diethyl benzyl amine, N-ethyl-N- methylbenzylamine, tribenzyl amine, cyclopentylamine, cyclohexylamine, cycloheptylamine, N-methylcyclopentylamine, N-ethylcyclohexyl amine, N-ethyl cycloheptylamine, dicyclohexylamine, N,N-dimethylcyclo pentylamine, N,N-dimethyl cyclohexylamine or N,N-diethylcycloheptylamine; and in step d), the alkali metal base is an alkali metal hydroxide, an alkali metal carbonate or an alkali metal bicarbonate, the solvent is a polar solvent and the calcium source is calcium chloride or calcium acetate.

4. The process of claim 2, wherein the compound of Formula-1 contains less than about 0.15 percent by area by HPLC of each of the impurities represented by the following structural formulas:

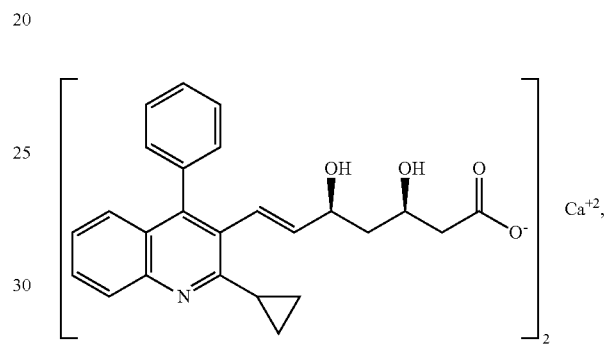

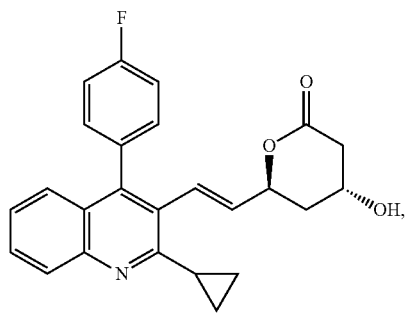

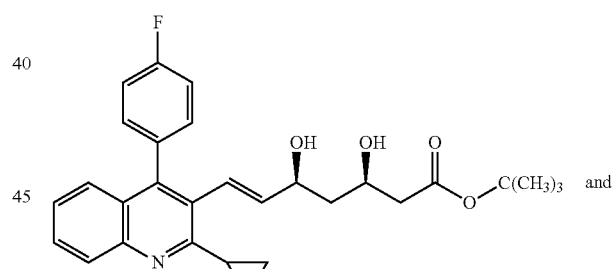

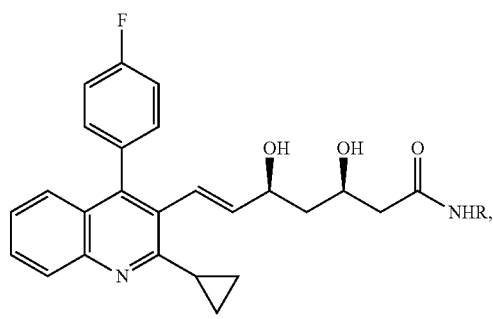

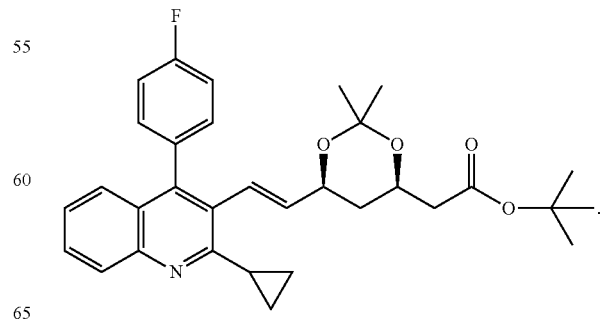

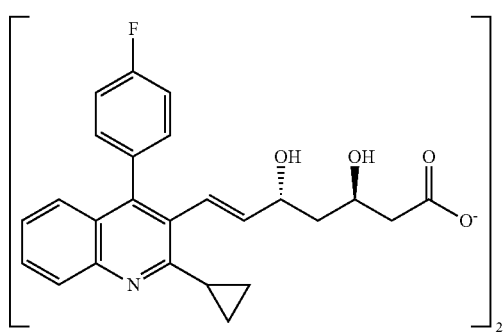

5. The process of claim 2, wherein the compound of Formula-1 is free of each of the impurities represented by the following structural formulas:

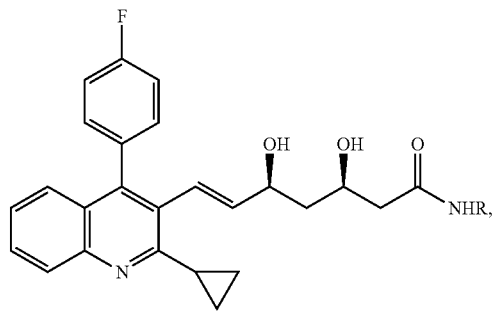

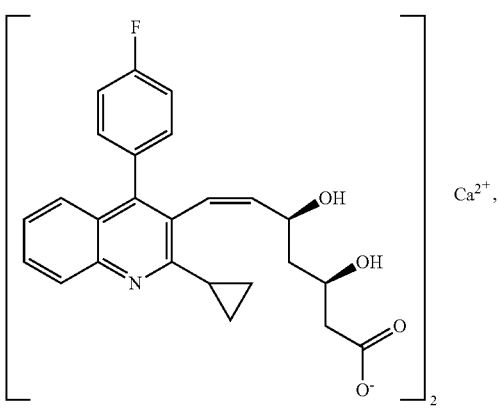

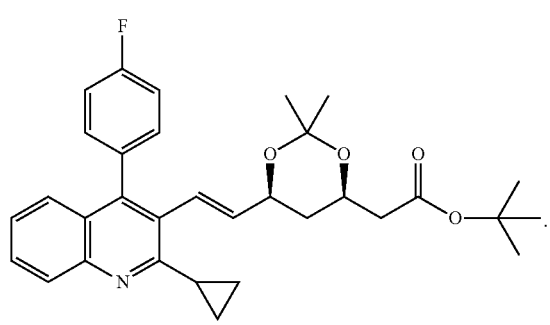

6. A process for the preparation of a compound of Formula-1,

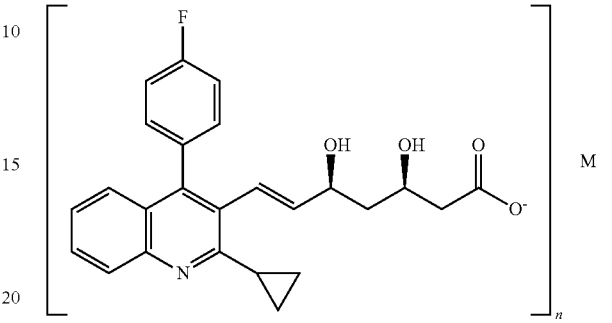

wherein M is $H^+$, $Na^+$ or $K^+$ and n is 1 or M is $Mg^{+2}$ or $Ca^{+2}$ and n is 2, comprising:

a) reacting a compound of Formula-2

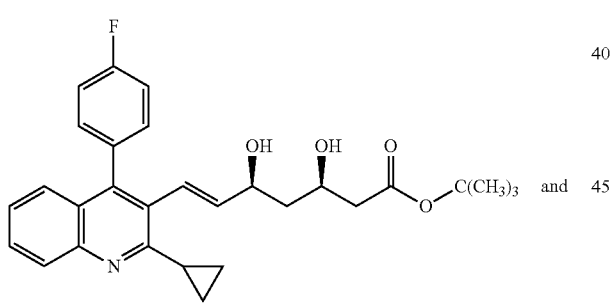

with a compound of Formula-3,

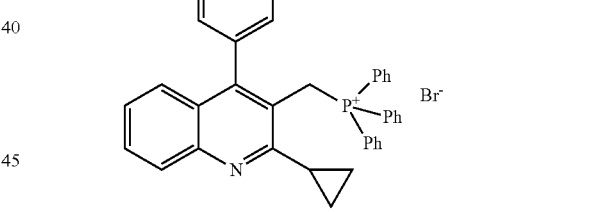

in the presence of a base in a solvent to obtain the compound of Formula-4,

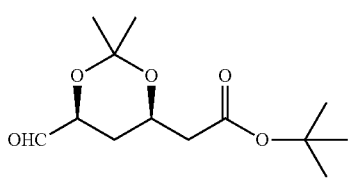

Formula-4

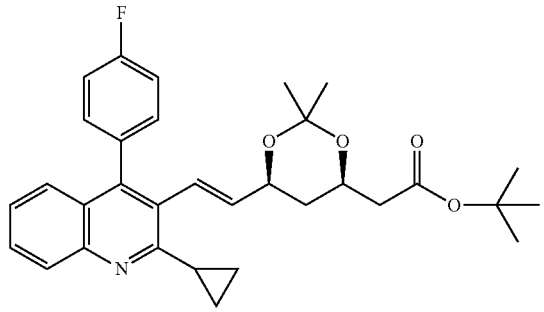

then recrystallizing the compound of Formula-4 from an alcoholic solvent, thereby removing Impurity A Impurity-A

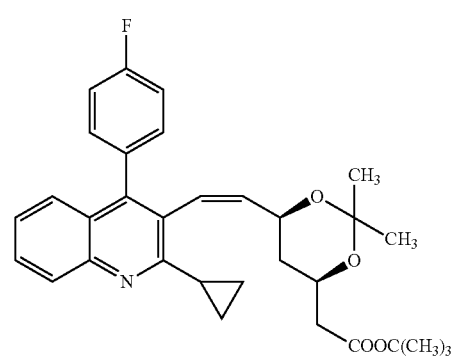

and obtaining the compound of Formula-4 as a crystalline solid;

b) reacting the recrystallized compound of Formula-4 with an acid in a solvent to obtain the compound of Formula-5, Formula-5

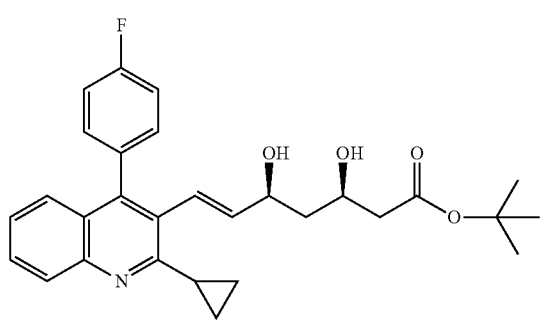

then recrystallizing the compound of Formula-5 from a hydrocarbon solvent, thereby removing Impurity B Impurity-B

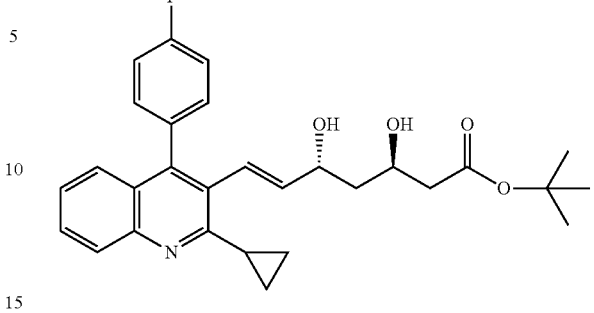

and obtaining the compound of Formula-5 as a crystalline solid; and c) hydrolyzing the recrystallized compound of Formula-5 with an alkali metal base in a solvent to provide the compound of Formula-1 wherein M is $Na^+$ or $K^+$ and n is 1.

7. The process of claim 6, wherein step c) further comprises treating the compound of Formula-1 wherein M is $Na^+$ or $K^+$ and n is 1 with a calcium source to obtain the compound of Formula-1 wherein M is $Ca^{2+}$ and n is 2.

8. The process of claim 7, wherein:
in step a), the base is an alkali metal carbonate and the solvent is a polar aprotic solvent;
in step b), the acid is hydrochloric acid, hydrobromic acid, acetic acid, sulfuric acid, oxalic acid, para toluene sulfonic acid, poly phosphoric acid, methane sulphonic acid, maleic acid, malic acid, fumaric acid or formic acid and the solvent is an alcoholic solvent or a hydrocarbon solvent; and
in step c), the alkali metal base is an alkali metal hydroxide, an alkali metal carbonate or an alkali metal bicarbonate, the solvent is a polar solvent and the calcium source is calcium chloride or calcium acetate.

9. The process of claim 7, wherein:
in step a), the base is potassium carbonate and the solvent is dimethylsulfoxide;
in step b), the acid is oxalic acid and the solvent is methanol; and
in step c), the alkali metal base is sodium hydroxide, the solvent is methanol and the calcium source is calcium chloride.

10. The process of claim 5, wherein the compound of Formula-1 contains less than about 0.15 percent by area by HPLC of each of the impurities represented by the following structural formulas:

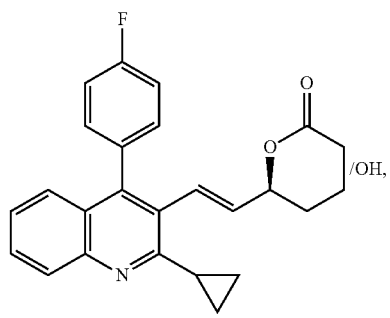

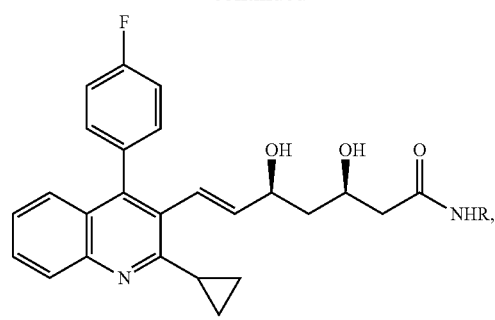
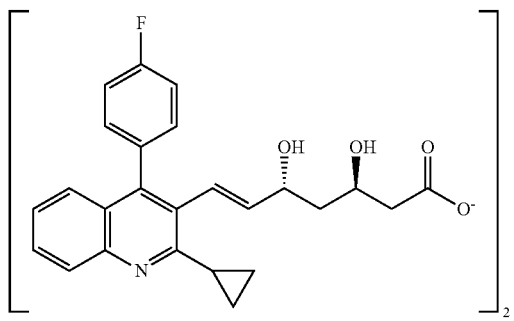
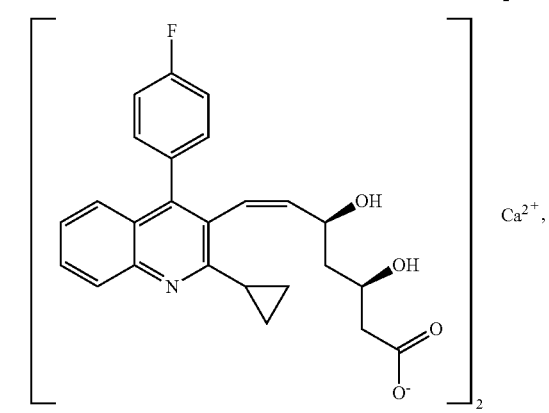
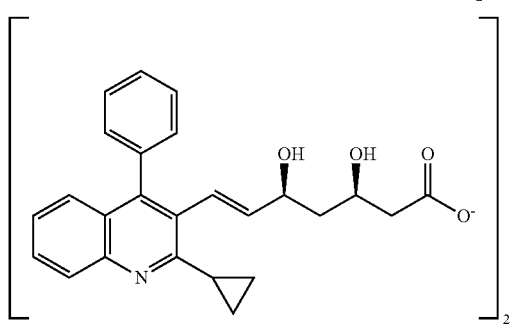
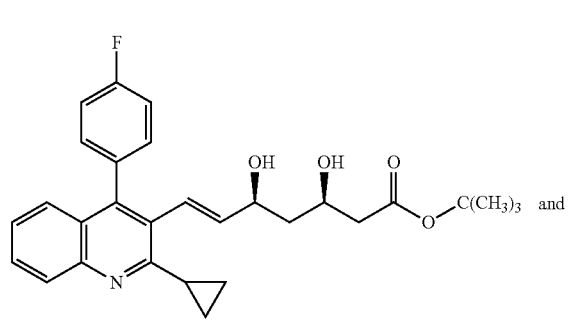
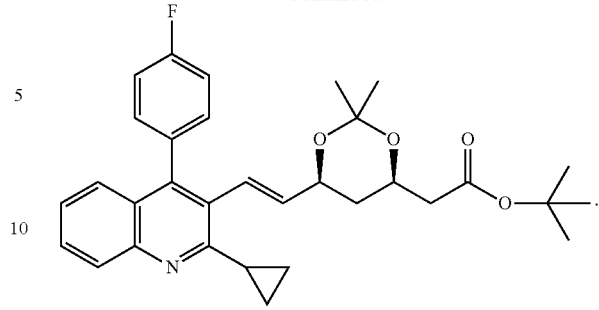
11. The process of claim 5, wherein the compound of Formula-1 is free of each of the impurities represented by the following structural formulas:
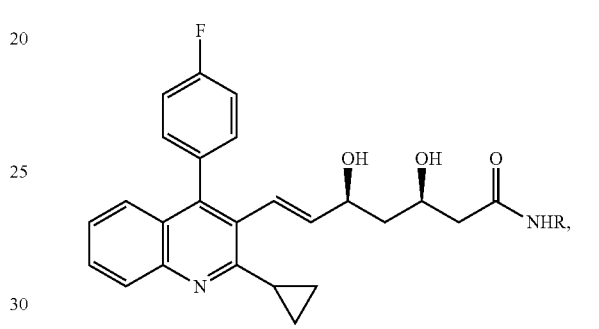
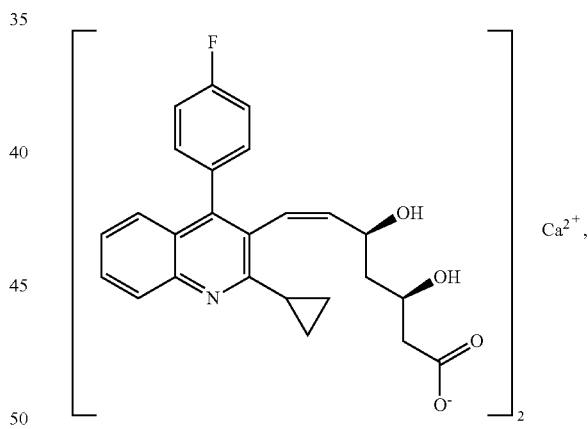
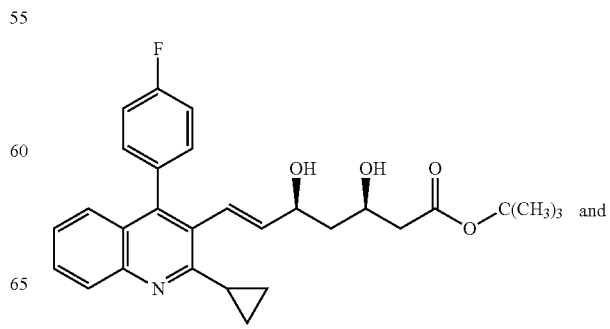

-continued

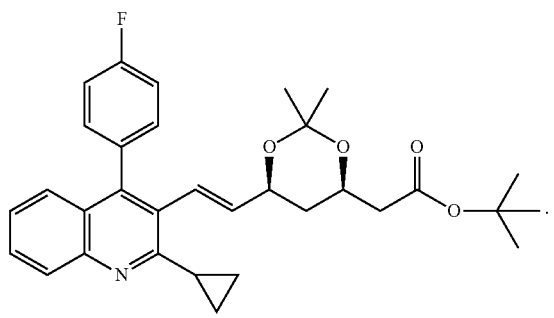

12. The process of claim 1, further comprising:
i) reacting cyclopropyl methyl ketone with dimethyl carbonate in the presence of a base in a solvent to provide a compound of Formula-8,

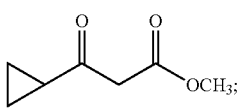

Formula-8 ii) reacting the compound of Formula-8 with a compound of Formula-9,

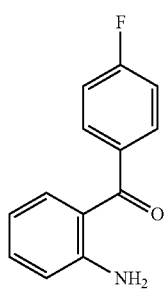

Formula-9 in the presence of an acid and, optionally, a solvent to produce a compound of Formula-10,

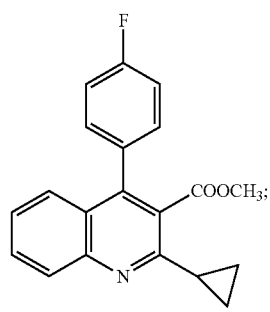

Formula-10 iii) reducing the compound of Formula-10 with a reducing agent in a solvent to obtain a compound of Formula-11,

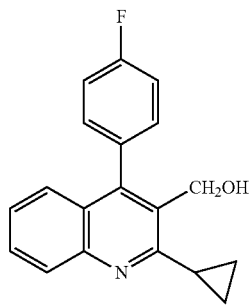

Formula-11 then recrystallizing the compound of Formula-11 from a second solvent; and iv) reacting the recrystallized compound of Formula-11 with phosphorous tribromide in a solvent, then treating with a triaryl or a trialkyl phosphine in a second solvent to provide the compound of Formula-2, then recrystallizing the compound of Formula-2 from a third solvent.

13. The process of claim 12, wherein:
in step i), the base is an alkali metal hydroxide, an alkali metal alkoxide, an alkali metal carbonate or an alkali metal bicarbonate and the solvent is a hydrocarbon solvent;
in step ii), the acid is sulfuric acid, poly phosphoric acid, methane sulfuric acid or para toluene sulfonic acid and the solvent is an alcoholic solvent or a hydrocarbon solvent;
in step iii), the reducing agent is DIBAL-H or vitride and the solvent is a hydrocarbon solvent; and
in step iv), the solvent is a chloro solvent, the triaryl phosphine is triphenyl phosphine and the trialkyl phosphine is tributyl phosphine.

14. The process of claim 13, wherein:
in step i), the base is potassium tertiary butoxide and the solvent is toluene;
in step ii), the acid is sulfuric acid and the solvent is methanol;
in step iii), the reducing agent is DIBAL-H and the solvent is toluene; and
in step iv), the solvent is methylene chloride and the triaryl or trialkyl phosphine is triphenyl phosphine.

15. The process of claim 12, wherein:
in step ii), the acid is sulfuric acid and the solvent is acetic acid.

16. The process according to claim 1, wherein step a) comprises:
i) reacting the compound of Formula-2 with the compound of formula-3 in the presence of an alkali metal carbonate in a polar aprotic solvent to provide the compound of Formula-4;
ii) heating the compound of Formula-4 in the alcoholic solvent to dissolve the compound of Formula-4, thereby obtaining a mixture;
iii) cooling the mixture to room temperature to obtain a crystalline form of the compound of Formula-4; and
iv) filtering, washing in the alcoholic solvent and drying the crystalline form of the compound of Formula-4,
wherein the crystalline form of the compound of Formula-4 is characterized by any of the following:
a) a powder x-ray diffractogram having peaks at about 7.89, 9.98, 11.53, 14.87, 15.96, 17.51, 18.17, 19.18, 19.99, 20.86, 24.76 and 27.68±0.2 degrees of 2 theta;

b) an IR spectrum having peaks at about 3061, 2991, 2976, 1721, 1601, 1488 and 1197 cm$^{-1}$; or c) a DSC thermogram having an endothermic peak at about 114.96° C.

17. The process of claim 16, wherein the alcoholic solvent in step a) is methanol, ethanol, isopropanol, butanol, or a mixture or aqueous solution thereof.

18. The process according to claim 1, wherein step b) comprises:
   i) reacting the recrystallized compound of Formula-4 with an acid in a solvent to provide a compound of Formula-5;
   ii) heating the compound of Formula-5 in the hydrocarbon solvent to dissolve the compound of Formula-5, thereby obtaining a mixture;
   iii) cooling the mixture to obtain a crystalline form of the compound of Formula-5; and
   iv) filtering, washing with a second solvent and drying the crystalline form of the compound of Formula-5,
wherein the crystalline form of the compound of Formula-5 is characterized by any of the following:
   a) a powder x-ray diffractogram having peaks at about 8.07, 10.19, 12.15, 14.52, 16.25, 17.45, 17.90, 19.49, 21.84 and 25.3±0.2 degrees of 2 theta;
   b) an IR spectrum having peaks at about 3413, 3005, 2971, 1733, 1604, 1512, 1489, 1152 and 766 cm$^{-1}$; or
   c) a DSC thermogram having an endothermic peak at about 121.78° C.

19. The process of claim 18, wherein the hydrocarbon solvent in step
   ii) of step b) is toluene, hexanes, heptanes, cyclohexane, or a mixture or aqueous solution thereof.

20. The process according to claim 1, wherein step c) comprises:
   i) hydrolyzing the recrystallized compound of Formula-5 with an alkali metal hydroxide in a solvent to obtain a carboxylic acid;
   ii) treating the carboxylic acid with methyl amine to obtain a compound of Formula-6a

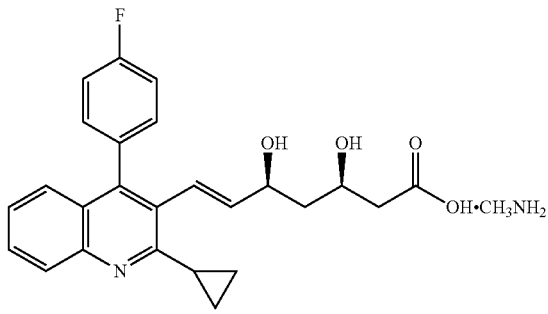

Formula-6a iii) adding acetonitrile to the compound of Formula-6a and cooling the resulting mixture to obtain a crystalline form of the compound of Formula-6a; and
   iv) filtering, washing with acetonitrile and drying the crystalline form of the compound of Formula-6a,
wherein the crystalline form of the compound of Formula-6a is characterized by any of the following:
   a) a powder x-ray diffractogram having peaks at about 8.61, 10.69, 16.11, 17.46, 18.13, 19.81, 20.97, 24.98, 25.76, 29.22 and 36.7±0.2 degrees of 2 theta;
   b) an IR spectrum having peaks at about 3423, 3085, 3004, 2937, 1627, 1601, 1489, 1271, 1121 and 763 cm$^{-1}$; or
   c) a DSC thermogram having an endothermic peak at about 151.16° C.

21. The process of claim 6, wherein:
   the compound is a compound of Formula-1 wherein M is H$^+$ and n is 1, and is characterized by an x-ray powder diffractogram having peaks at about 5.56, 10.57, 11.73, 13.15, 18.17, 19.36, 20.01, 21.98, 24.18, 24.73, 31.85 and 45.59±0.2 degrees of 2 theta, and
   the alkali metal base in step c) is an alkali metal hydroxide, the process further comprising:
   i) acidifying the product of step c) with an acid to obtain a crystalline form of a compound of Formula-1, wherein M is H$^+$ and n is 1;
   ii) filtering the crystalline form of the compound of Formula-1, wherein M is H$^+$ and n is 1, and slurrying the same in water; and
   iii) drying the crystalline form of the compound of Formula-1, wherein M is H$^+$ and n is 1.

22. The process of claim 7, wherein the compound is a compound of Formula-1 wherein M is H$^+$ and n is 1, and is characterized by an x-ray powder diffractogram having peaks at about 5.56, 10.57, 11.73, 13.15, 18.17, 19.36, 20.01, 21.98, 24.18, 24.73, 31.85 and 45.59±0.2 degrees of 2 theta,
   the process further comprising:
   a) suspending the compound of Formula-1, wherein M is Ca$^{2+}$ and n is 2 in a solvent, to obtain a mixture;
   b) acidifying the mixture with an acid;
   c) stirring the mixture to obtain a crystalline form of the compound of Formula-1, wherein M is H$^+$ and n is 1;
   d) filtering the crystalline form of the compound of Formula-1, wherein M is H$^+$ and n is 1 and washing the same with water; and
   e) drying the crystalline form of the compound of Formula-1, wherein M is H$^+$ and n is 1.

* * * * *

UNITED STATES PATENT AND TRADEMARK OFFICE
CERTIFICATE OF CORRECTION

PATENT NO.       : 8,487,105 B2
APPLICATION NO.  : 13/145089
DATED            : July 16, 2013
INVENTOR(S)      : Manne Satyanarayana Reddy et al.

Page 1 of 1

It is certified that error appears in the above-identified patent and that said Letters Patent is hereby corrected as shown below:

In the Claims

In column 31, Claim 1, lines 16-17 delete "a second" and insert --an alcoholic--.

In column 38, Claim 10, lines 55-66 delete " 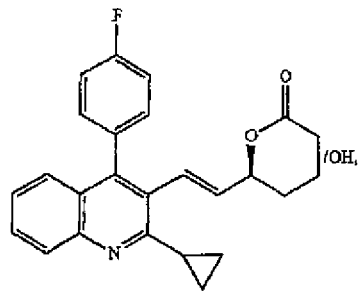 "

and insert -- 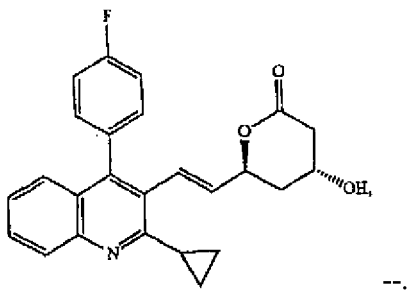 --.

Signed and Sealed this
Fifteenth Day of October, 2013

Teresa Stanek Rea
*Deputy Director of the United States Patent and Trademark Office*